(12) United States Patent
Sanger

(10) Patent No.: US 12,257,143 B2
(45) Date of Patent: Mar. 25, 2025

(54) INTRAOCULAR LENS

(71) Applicant: Hoya Medical Sinapore Pte. Ltd., Singapore (SG)

(72) Inventor: Demas Sanger, Fukaya (JP)

(73) Assignee: Hoya Medical Singapore Pte. Ltd., Singapore (SG)

( * ) Notice: Subject to any disclaimer, the term of this patent is extended or adjusted under 35 U.S.C. 154(b) by 305 days.

(21) Appl. No.: 17/779,311

(22) PCT Filed: Nov. 10, 2020

(86) PCT No.: PCT/JP2020/041882
§ 371 (c)(1),
(2) Date: May 24, 2022

(87) PCT Pub. No.: WO2021/111821
PCT Pub. Date: Jun. 10, 2021

(65) Prior Publication Data
US 2022/0401210 A1 Dec. 22, 2022

(30) Foreign Application Priority Data
Dec. 5, 2019 (JP) .................... 2019-220380

(51) Int. Cl.
*A61F 2/16* (2006.01)
*G02C 7/02* (2006.01)

(52) U.S. Cl.
CPC ............. *A61F 2/16* (2013.01); *A61F 2/164* (2015.04); *G02C 7/02* (2013.01)

(58) Field of Classification Search
CPC .......... A61F 2/16; A61F 2/164; A61F 2/1618; G02C 7/02; G02C 7/042; G02C 7/044
See application file for complete search history.

(56) References Cited

U.S. PATENT DOCUMENTS 4,504,982 A 3/1985 Burk
4,752,123 A 6/1988 Blaker
(Continued)

FOREIGN PATENT DOCUMENTS

EP 2403429 B1 2/2017
JP 60-085744 A 5/1985
(Continued)

OTHER PUBLICATIONS

Boettner et al., *Transmission of the Ocular Media*, Investigative Ophthalmology vol. 1, No. 6, pp. 776-783 (Dec. 1962).
(Continued)

*Primary Examiner* — Collin X Beatty
(74) *Attorney, Agent, or Firm* — Henricks Slavin LLP

(57) ABSTRACT

Provided are an intraocular lens and a technique associated therewith, wherein an average value (exceeding 0 D) of base difference values within a first region from a lens center O to a position r1 of a first boundary is greater than 5 times an average value (exceeding 0 D) of base difference values within the first region from a lens center O of a virtual spherical lens having a base power at the lens center O to the position r1, a second region has a power resulting from adding one or more positive constant powers to a reference aspheric power, in a third region, the power is reduced so as to provide a negative longitudinal spherical aberration that cancels at least part of a positive longitudinal spherical aberration caused by a cornea, and a second step value is greater than a first step value.

16 Claims, 21 Drawing Sheets

(56) References Cited

U.S. PATENT DOCUMENTS

| | | |
|---|---|---|
| 4,778,462 A | 10/1988 | Grendahl |
| 4,795,462 A | 1/1989 | Grendahl |
| 4,813,955 A | 3/1989 | Achatz |
| 5,139,519 A | 8/1992 | Kalb |
| 5,225,858 A | 7/1993 | Portney |
| 5,517,260 A | 5/1996 | Glady et al. |
| 5,812,235 A * | 9/1998 | Seidner ................ G02C 7/044 351/159.1 |
| 5,919,229 A | 7/1999 | Portney |
| 6,015,435 A | 1/2000 | Valunin et al. |
| 6,145,987 A | 11/2000 | Baude et al. |
| 6,210,005 B1 | 4/2001 | Portney |
| 6,457,826 B1 | 10/2002 | Lett |
| 6,537,317 B1 * | 3/2003 | Steinert ................ G02C 7/044 623/6.24 |
| 6,576,012 B2 * | 6/2003 | Lang ...................... G02C 7/027 623/6.28 |
| 8,079,704 B2 * | 12/2011 | Sanger .................. G02C 7/042 351/159.42 |
| 8,623,084 B2 | 1/2014 | Shoji et al. |
| 8,647,383 B2 | 2/2014 | Sanger et al. |
| 8,672,474 B2 * | 3/2014 | Lindacher ............. G02C 7/044 351/159.13 |
| 8,777,415 B2 * | 7/2014 | Back ...................... G02C 7/042 351/159.05 |
| 9,952,449 B2 * | 4/2018 | Goto ...................... G02C 7/041 |
| 10,191,303 B2 * | 1/2019 | de Juan, Jr. ........... G02C 7/049 |
| 11,529,228 B2 * | 12/2022 | Liang .................. A61F 9/00808 |
| 2002/0016630 A1 | 2/2002 | Lang |
| 2002/0044255 A1 | 4/2002 | Ye |
| 2003/0081171 A1 | 5/2003 | Griffin |
| 2004/0106992 A1 | 6/2004 | Lang et al. |
| 2004/0167623 A1 | 8/2004 | Peyman |
| 2005/0068494 A1 * | 3/2005 | Griffin .................. G02C 7/044 351/159.41 |
| 2007/0258143 A1 | 11/2007 | Portney |
| 2008/0084534 A1 | 4/2008 | Lindacher et al. |
| 2009/0270984 A1 | 10/2009 | Sanger et al. |
| 2010/0057202 A1 * | 3/2010 | Bogaert ................ A61F 2/1613 623/6.27 |
| 2010/0321632 A1 | 12/2010 | Sanger |
| 2012/0327363 A1 | 12/2012 | Wooley et al. |
| 2014/0309736 A1 | 10/2014 | Sanger et al. |
| 2019/0142576 A1 * | 5/2019 | Goldshleger ........... A61L 27/18 623/6.24 |

FOREIGN PATENT DOCUMENTS

| | | |
|---|---|---|
| JP | 05-021922 U | 3/1993 |
| JP | 06-508279 A | 9/1994 |
| JP | 2000-122007 A | 4/2000 |
| JP | 2003-532157 A | 10/2003 |
| JP | 2006-014818 A | 1/2006 |
| JP | 2006-139292 A | 6/2006 |
| JP | 2007-330478 A | 12/2007 |
| WO | WO 9222264 A | 12/1992 |
| WO | WO 9726843 A1 | 7/1997 |
| WO | WO 9744698 A1 | 11/1997 |
| WO | WO 0184214 A2 | 11/2001 |
| WO | WO 0189424 A1 | 11/2001 |
| WO | WO 2005046527 A2 | 5/2005 |
| WO | WO 2008078804 A1 | 7/2008 |
| WO | WO 2009153873 A1 | 12/2009 |
| WO | WO-2010100523 A1 * | 9/2010 ........... A61F 2/1613 |

OTHER PUBLICATIONS

PCT International Search Report dated Jan. 12, 2021 for PCT App. Ser. No. PCT/JP2020/041882.

PCT International Preliminary Report on Patentability dated May 17, 2022 for PCT App. Ser. No. PCT/JP2020/041882.

* cited by examiner

EM - IOL

(a) DISTANCE 6 m,
PUPIL DIAMETER 2.5 mm (b) DISTANCE 6 m,
PUPIL DIAMETER 3 mm (c) DISTANCE 1.2 m,
PUPIL DIAMETER 3 mm (d) DISTANCE 1.2 m,
PUPIL DIAMETER 3.5 mm

EDOF (a) DISTANCE 6 m,
PUPIL DIAMETER 2.5 mm (b) DISTANCE 6 m,
PUPIL DIAMETER 3 mm (c) DISTANCE 65 cm,
PUPIL DIAMETER 3 mm (d) DISTANCE 65 cm,
PUPIL DIAMETER 3.5 mm

Multifocal lens (a) DISTANCE 6 m, PUPIL DIAMETER 2.5 mm (b) DISTANCE 6 m, PUPIL DIAMETER 3 mm (c) DISTANCE 40 cm, PUPIL DIAMETER 3 mm (d) DISTANCE 40 cm, PUPIL DIAMETER 3.5 mm

INTRAOCULAR LENS

TECHNICAL FIELD

The present invention relates to an intraocular lens.

BACKGROUND ART

Intraocular lenses are known to serve the function of correcting visual acuity after a clouded crystalline lens due to cataract has been removed. For example, when a crystalline lens has been clouded due to cataract, the visual acuity is restored by a surgical procedure by inserting an artificial intraocular lens into the lens capsule to replace the clouded lens.

Paragraph [0007] of Patent Document 1 describes, as a problem to be solved, obtaining an intraocular lens in which deterioration in contrast is suppressed even if the optical axis of an intraocular lens is decentered from the optical axis of an eyeball when the intraocular lens is inserted into the eye, while the advantage of a conventional aberration compensation type intraocular lens that is the image can be clearly seen is maintained.

In order to solve that problem, [Claim 1] and so forth of Patent Document 1 describes that deterioration in contrast occurring when the optical axis of the intraocular lens inserted into an eye is decentered from the optical axis of an eyeball is suppressed by employing such a power distribution as having at least one positive power deviation region having a larger power than that represented by a reference power distribution and at least one negative power deviation region having a smaller power than that represented by the reference power distribution in a region in the vicinity of the center of the intraocular lens, assuming that the reference power distribution being set to cancel a spherical aberration of the cornea when the intraocular lens is inserted into the eye.

CITATION LIST

Patent Document

Patent Document 1: JP 2007-330478A

SUMMARY OF INVENTION

Technical Problem

With the widespread use of personal computers and mobile phones, the importance of correcting the visual acuity for near to intermediate vision is increasing. More specifically, there is an increasing demand for effortlessly achieving a good visual field when viewing an object not only at least at one distance from near to intermediate vision, but also at distances in front and in rear thereof.

An object of the present invention is to provide an intraocular lens capable of correcting the visual acuity for far vision and effortlessly achieving a good visual field when viewing an object not only at least at one distance from near to intermediate vision, but also at distances in front and in rear thereof, and a technique associated therewith.

Solution to Problem

A first aspect of the present invention is an intraocular lens including at least three visual acuity correction regions that are concentric with a lens center O at which a predetermined base power is set, and that are adjacent to each other, wherein the visual acuity correction regions are set as a first region including the lens center O, and a second region and a third region disposed in this order radially from the first region, where r1 is a position of a first boundary between the first region and the second region, and r2 is a position of a second boundary between the second region and the third region, as viewed radially from the lens center O, the first region is a region for correcting a visual acuity for far vision or a visual acuity for vision between far vision and intermediate vision, the second region is a region for correcting a visual acuity for intermediate vision or a visual acuity for near vision, the third region is a region for correcting the visual acuity for far vision, a change in power is discontinuous on the first boundary and the second boundary, a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary, an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O to the position r1, the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by a cornea, the power is reduced in the third region so as to provide a negative longitudinal spherical aberration that cancels at least part of the positive longitudinal spherical aberration caused by the cornea, a second step value constituted by a value obtained by subtracting a power $P_{B2Low}$ of the third region from a power $P_{B2High}$ of the second region on the second boundary is greater than a first step value constituted by a value obtained by subtracting the power $P_{B1Low}$ of the first region from the power $P_{B1High}$ of the second region on the first boundary, and the power $P_{B2High}$ of the second region on the second boundary is greater than the base power, and the power $P_{B2Low}$ of the third region on the second boundary is less than the base power.

A second aspect of the present invention is an intraocular lens including at least three visual acuity correction regions that are concentric with a lens center O at which a predetermined base power is set, and that are adjacent to each other, wherein the visual acuity correction regions are set as a first region including the lens center O, and a second region and a third region disposed in this order radially from the first region, when r1 is a position of a first boundary between the first region and the second region, r2 is a position of a second boundary between the second region and the third region, and r3 is a position of an outermost edge of the third region, as viewed radially from the lens center O, the first region is a region for correcting a visual acuity for far vision or a visual acuity for vision between far vision and intermediate vision, the second region is a region for correcting a visual acuity for intermediate vision or a visual acuity for near vision, the third region is a region for correcting the visual acuity for far vision, a change in power is discontinuous on the first boundary and the second boundary, a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary, an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O from to the position r1, a power $P_{B2High}$ of the second region on the second boundary is greater than the base power, and a power $P_{B2Low}$ of the third region on the second boundary is less than the base power, and the first region, the second region, and the third region are shaped such that a total power T obtained by summing up a refractive power of the cornea and a power of the intraocular lens increases in an area from the lens center O to the position r1 of the first boundary, the total power T is equal to a total power $T_O$ at the lens center O in an area from the position r2 of the second boundary to the position r3 of the outermost edge of the third region, and the total power T is equal to a value resulting from adding one or more positive constant powers to the total power To in an area from the position r1 of the first boundary to the position r2 of the second boundary.

A third aspect of the present invention is n intraocular lens including at least three visual acuity correction regions that are concentric with a lens center O at which a predetermined base power is set, and that are adjacent to each other, wherein the visual acuity correction regions are set as a first region including the lens center O, and a second region and a third region disposed in this order radially from the first region, when r1 is a position of a first boundary between the first region and the second region, and r2 is a position of a second boundary between the second region and the third region, as viewed radially from the lens center O, the first region is a region for correcting a visual acuity for far vision or a visual acuity for vision between far vision and intermediate vision, the second region is a region for correcting a visual acuity for intermediate vision or a visual acuity for near vision, the third region is a region for correcting the visual acuity for far vision, a change in power is discontinuous on the first boundary and the second boundary, a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary, an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O to the position r1, a power $P_{B2High}$ of the second region on the second boundary is greater than the base power, and a power $P_{B2Low}$ of the third region on the second boundary is less than the base power, and the first region and the second region are sized such that, assuming that all light rays related to a spatial frequency of 50 line pairs/mm pass through a virtual cornea and the intraocular lens, a depth of focus is substantially the same as or deeper than a depth of focus of the virtual spherical lens for an aperture diameter of 2.5 mm or less, a depth of focus is at least 10% deeper than the depth of focus of the virtual spherical lens for an aperture diameter of 3 to 4 mm, and a contrast peak is present at a defocus value in a range from –0.25 D to 0.25 D for an aperture diameter of 5 mm or more. The defocus value is plotted on the horizontal axis of a graph of a through focus MTF (=through focus response (TFR)).

A fourth aspect of the present invention is an intraocular lens including at least three visual acuity correction regions that are concentric with a lens center O at which a predetermined base power is set, and that are adjacent to each other, wherein the visual acuity correction regions are set as a first region including the lens center O, and a second region and a third region disposed in this order radially from the first region, when r1 is a position of a first boundary between the first region and the second region, and r2 is a position of a second boundary between the second region and the third region, as viewed radially from the lens center O, the first region is a region for correcting a visual acuity for far vision or a visual acuity for vision between far vision and intermediate vision, the second region is a region for correcting a visual acuity for intermediate vision or a visual acuity for near vision, the third region is a region for correcting the visual acuity for far vision, a change in power is discontinuous on the first boundary and the second boundary, a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary, an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O to the position r1, a power $P_{B2High}$ of the second region on the second boundary is greater than the base power, and a power $P_{B2Low}$ of the third region on the second boundary is less than the base power, and the power is reduced in the third region so as to provide a negative longitudinal spherical aberration that cancels at least part of a positive longitudinal spherical aberration caused by a cornea, a sag value of an anterior surface, a sag value of a posterior surface, or sag values of both the anterior surface and the posterior surface of the intraocular lens are represented by the following polynomial equation:

$$z = \frac{cr^2}{1+\sqrt{1-(1+k)c^2r^2}} + a_1 r^2 + a_2 r^4 + a_3 r^6 + a_4 r^8 + \ldots + a_n r^{2n} \quad \text{[Math. 1]}$$

z: sag value
c: curvature of lens center (=1/R [m])
k: conic constant
r: distance from lens center, i.e., radius
$a_1, a_2, \ldots, a_n$: coefficient the power of each of the regions is represented by the following polynomial equation:

$$P_i = c_{0,i} + c_{1,i} r^1 + c_{2,i} r^2 + c_{3,i} r^3 + c_{4,i} r^4 + \ldots + c_{n,i} r^n \quad \text{[Math. 2]}$$

$P_i$: power of i-th region
r: distance from lens center, i.e., radius
$c_{0,i}, c_{1,i}, \ldots, c_{n-1,i}, c_{n,i}$: coefficient the power of the second region is represented by the following equation:

$$P_2 = A + P_3 \quad \text{[Math. 3]}$$

$P_2$: power of second region
$P_3$: power of third region
A: addition power to reference aspheric power A is a value obtained by subtracting, from the power of the second region at a predetermined position r within the second region, a reference aspheric power, at the position r, of a virtual aspheric lens that has a base power at the lens center O, and that cancels the whole of the positive longitudinal spherical aberration caused by the cornea, and the power of the third region is represented by the following polynomial equation:

$$P_3 = c_{0,3} + c_{1,3} r^1 + c_{2,3} r^2 + c_{3,3} r^3 + c_{4,3} r^4 + \ldots + c_{n,3} r^n \quad \text{[Math. 4]}$$

$P_3$: power of third region
r: distance from lens center, i.e., radius
$c_{0,3}, c_{1,3} \ldots, c_{n-1,3} c_{n,3}$: coefficient A fifth aspect of the present invention is an invention according to the fourth aspect, wherein, in an area from the position r1 of the first boundary to the position r2 of the second boundary, a total power T obtained by summing up the refractive power of the cornea and the power of the intraocular lens is constituted by one or more constant values, and a visual acuity when viewing an object at one or more distances from an intermediate vision distance to a near vision distance is corrected using the total power T.

A sixth aspect of the present invention is an invention according to any one of the third to fifth aspects, wherein the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by a cornea.

A seventh aspect of the present invention is an invention according to any one of the first to sixth aspects, wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

Other aspects of the present invention are listed below.

r1 and r2 may be set such that 0.7 mm≤r1≤1.3 mm, and 1.1 mm≤r2≤2.0 mm.

The area ratio between the first region and the second region in a plan view may be set from 25:75 to 75:25, and the area ratio between the second region and the third region in a plan view may be set from 30:70 to 5:95.

As for whether or not a change in power is "steep" when the change is substantially discontinuous, the change in power may be regarded as steep when it has a degree of change of 100 D/mm or more, for example.

Preferably, the power continuously increases in the first region.

Preferably, the power continuously decreases in the second region.

Preferably, the power continuously decreases in the third region.

Preferably, the total power T obtained by summing up the refractive power of the cornea and the power of the intraocular lens continuously increases in an area from the lens center O to the position r1 of the first boundary.

The average value of the base difference values within the first region from the lens center O to the position r1 of the first boundary is preferably greater than or equal to 5 times, and more preferably greater than or equal to 10 times the average value of the base difference values within the first region from the lens center O of a virtual spherical lens having a base power at the lens center O to the position r1.

The second step value is preferably greater than or equal to 1.25 times the first step value.

Using <Condition g> in addition to <Condition a> and <Condition b> described in Embodiment 2 below can also provide the effects of the present invention, and can constitute an invention.

Using only <Condition h> described in Embodiment 3 below can also provide the effects of the present invention, and can constitute an invention.

Using only <Condition i> described in Embodiment 4 below can also provide the effects of the present invention, and can constitute an invention.

<Condition e> described in Embodiment 1 below can be deleted to expand the technical scope.

The term "power equal to a reference aspheric power" indicates that the deviation from the reference aspheric power is less than ±0.30 D (preferably less than ±0.15 D) at a predetermined distance from the lens center O.

The term "power resulting from adding one or more positive constant powers to a reference aspheric power" indicates that the deviation from a plot resulting from adding one or more positive constant powers to the reference aspheric power is less than ±0.30 D (preferably less than ±0.15 D) at a predetermined distance from the lens center O.

When there are a plurality of positive constant powers, a constant value added in an area of the second region that includes the position r1 is greater than a constant value added in an area that is adjacent to the aforementioned area and that is located away from the lens center O. When there are three or more different positive constant powers, a constant value added in the area located away is greater than a constant value added in an area that is adjacent to the area located away and that is located farther away from the lens center O. That is, it is preferable that, in the second region, the constant value added decreases as the distance from the lens center O increases.

The technical idea of the present invention is also applicable to a contact lens. When an expression encompassing a contact lens and an intraocular lens is defined as an ophthalmic lens, the term "intraocular lens" described herein may be replaced by the term "ophthalmic lens".

The technical idea of the present invention is also applicable to a designing method or a manufacturing method of an intraocular lens.

The intraocular lens may be an ophthalmic lens wherein a depth of focus in a small aperture diameter region that is a region in which the lens center O is disposed and that corresponds to an aperture diameter a1 is substantially the same as or deeper than a depth of focus of a small aperture diameter region of a virtual spherical lens having a curvature at a lens center, a medium aperture diameter region that is covered when the aperture diameter increases from the aperture diameter a1 to an aperture diameter a2 has a power corresponding to a predetermined finite distance (which can be set to a plurality of different distances) when the ophthalmic lens is being worn, and a large aperture diameter region that is covered when the aperture diameter increases from the aperture diameter a2 to an aperture diameter a3 has a power corresponding to far vision, and includes a negative longitudinal spherical aberration that cancels at least part of a positive longitudinal spherical aberration caused by the cornea when the ophthalmic lens is being worn.

The aperture diameters a1, a2, and a3 may be the aperture diameters described as the effects of Embodiment 1. That is, the aperture diameters a1, a2, and a3 may be set within a range that satisfies a1≤2.5 mm, 3 mm≤a2≤4 mm, and a3≥5 mm.

The small aperture diameter region corresponding to the aperture diameter a1 corresponds to the first region in the embodiments. The medium aperture diameter region that is covered when the aperture diameter increases from the aperture diameter a1 to the aperture diameter a2 corresponds to the second region in the embodiments. The large aperture diameter region that is covered when the aperture diameter increases from the aperture diameter a2 to the aperture diameter a3 corresponds to the third region in the embodiments.

Advantageous Effects of Invention

According to the present invention, it is possible to correct the visual acuity for far vision, and effortlessly provide a good visual field when viewing an object not only at least at one distance from near to intermediate vision, but also at distances in front and in rear thereof.

DESCRIPTION OF EMBODIMENTS

Definitions, Etc.

As for configurations not described below, known configurations may be used as appropriate. In particular, the content (in particular a supporting part) described in a document (WO 2009/153873) disclosed by the present inventor may be applied to the present embodiment.

The term "to" as used in the present specification refers to a predetermined value or more and a predetermined value or less.

The lens body of an intraocular lens described in the present specification has two surfaces that oppose each other.

A surface of the lens body that is in contact with a posterior capsule when the intraocular lens is inserted into a lens capsule can be referred to as a posterior surface, a retina-side surface, or a retina-side surface in the optical axis direction. In the present specification, the term "posterior surface" is mainly used. The other side of the lens body can be referred to as an anterior surface, a cornea-side surface, or a cornea-side surface in the optical axis direction. In the present specification, the term "anterior surface" is mainly used. The optical axis direction is also the lens thickness direction, which is a direction extending from the posterior surface toward the anterior surface, or a direction opposite thereto. The optical axis direction is the z-axis direction.

Although infinity is illustrated as an example of far vision in the present embodiment, it is also possible to assume a case where an object at a finite distance (1.5 m or less (far distance)), rather than infinity, is viewed.

For intermediate vision, it is possible to assume a case where an object at 1.5 m to 50 cm (intermediate distance) is viewed.

For near vision, it is possible to assume a case where an object at 50 cm or less (near distance) is viewed.

In any case, a case where a distance farther than near vision is viewed is referred to as intermediate vision, and a case where a distance farther than intermediate vision is viewed is referred to as far vision.

The lens center O refers to a geometrical center or an optical center of the intraocular lens. In the present specification, a case where the geometrical center coincides with the optical center is illustrated. Also, a refractive power at the lens center O is referred to as a base power. The base power refers to a refractive power required for correcting far vision of a conventional intraocular lens.

Embodiment 1

An embodiment of the present invention will be described in detail below with reference the drawings.

Figure 1:
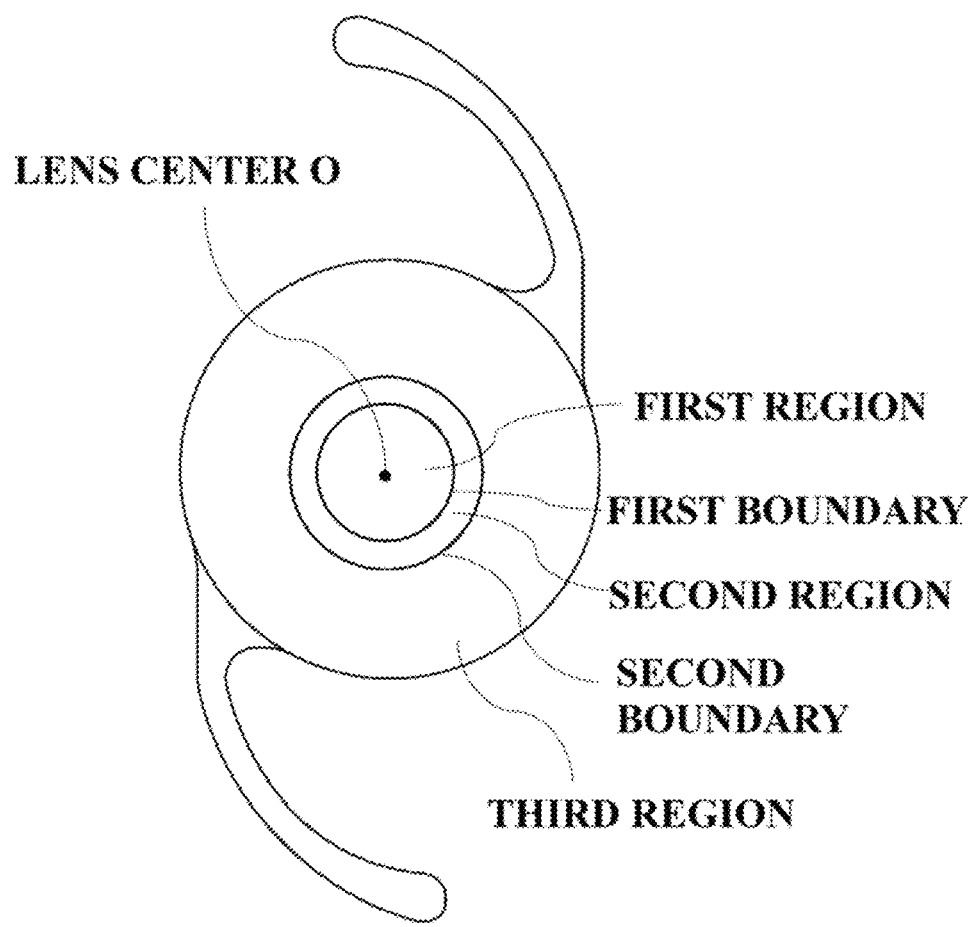
FIG. 1 is a schematic plan view showing an intraocular lens according to Embodiment 1.

FIG. 1 is a schematic plan view showing an intraocular lens according to Embodiment 1.

As shown in FIG. 1, the intraocular lens according to Embodiment 1 (and other aspects described in the present specification) includes a lens body having a lens function, and a supporting part that supports the lens body within a lens capsule, as in the case of a conventional intraocular lens. In addition, as shown in FIG. 1, in Embodiment 1 (and other aspects described in the present specification), a case where the entire lens body constitutes an optical part having a lens function is illustrated. That is, the entire lens body includes a first region (zone 1), a second region (zone 2), and a third region (zone 3), which will be described later.

In Embodiment 1, the intraocular lens is defined using a refractive power with respect to a distance radially away from the lens center O.

First, an aspect of the intraocular lens according to Embodiment 1 (and other aspects described in the present specification) includes at least three visual acuity correction regions that are concentric with a lens center O at which a predetermined base power is set, and that are adjacent to each other. The visual acuity correction regions are set as a first region including the lens center O, and a second region and a third region disposed in this order radially from the first region. Also, r1 is set as the position of a first boundary (boundary 1) between the first region and the second region, r2 is set as the position of a second boundary (boundary 2) between the second region and the third region, and r3 is set as the position of an outermost edge of the third region, as viewed radially from the lens center O.

As shown in FIG. 1, in a plan view, the first region has a circular shape, the second region has a small annular shape, and the third region has a large annular shape. An elliptic shape and/or an elliptic annular shape may be used in place of a circular shape and/or an annular shape. For elliptic shapes, a major diameter or a minor diameter may be used for the position r1 of the first boundary and the position r2 of the second boundary. Preferably, the following conditions are satisfied for both cases.

As for the conditions listed below, each of the conditions alone contributes to the effects of the present invention. On the other hand, it is a combinations of the conditions that constitutes an aspect of the present invention, and the effects of the present invention are achieved thereby. The following conditions are itemized merely for the sake of ease of description. The technical idea of the present invention has been conceived not from the idea of simply combining the following conditions, but as a result of intensive studies for solving the problem to be solved by the present invention.

Figure 2:
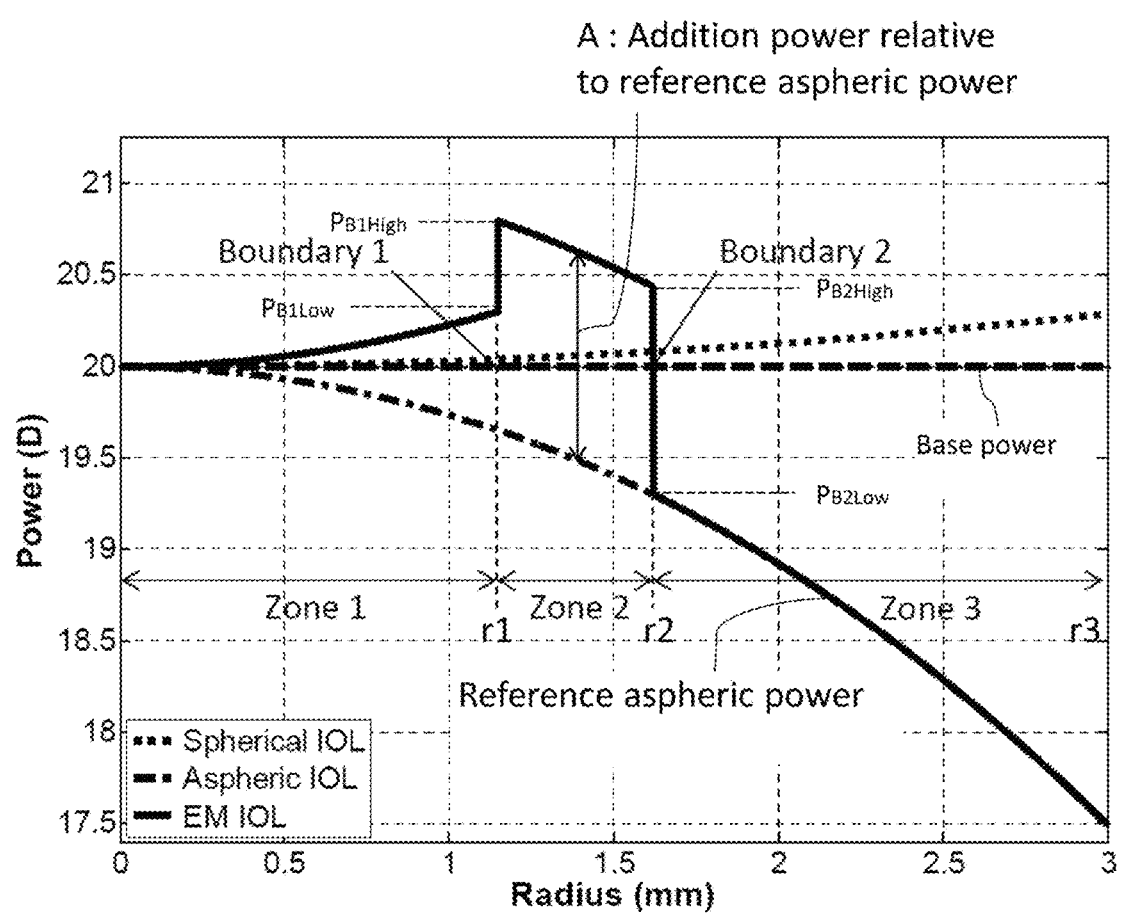
FIG. 2 is a plot showing a refractive power (vertical axis) provided by an optical part of the intraocular lens, versus a distance (horizontal axis) from a lens center O.

FIG. 2 is a plot showing a refractive power (vertical axis) provided by the intraocular lens, versus a distance (horizontal axis) from the lens center O. The distance from the lens center O is also called a radius.

The solid line is the plot of the intraocular lens according to Embodiment 1 (and other aspects described in the present specification).

The dotted line is a plot of a virtual spherical lens having a base power (broken line) at the lens center O.

The dashed dotted line is a plot of a virtual aspheric lens that has a base power at the lens center O, and that cancels the whole of a positive longitudinal spherical aberration caused by a cornea. This plot is also referred to as a reference aspheric power.

A longitudinal spherical aberration is a spherical aberration in a direction extending in a radial manner, or in other words, a radial (meridional) direction, as viewed from the lens center O. In this case, a spherical aberration in a circumferential (sagittal) direction perpendicular to the radial direction is a lateral spherical aberration.

The cornea has a positive refractive power. The spherical aberration increases as the distance from the center of the cornea increases. That is, the dashed dotted line indicating the reference aspheric power plots a virtual aspheric lens that theoretically cancels the whole of a positive longitudinal spherical aberration caused by the cornea.

Hereinafter, the meanings of the various types of lines are the same as those described thus far.

An IOL of an aspheric optical design is designed so as to correct or reduce the whole or part of the spherical aberration of the cornea. The degree to which the spherical aberration of the cornea is to be reduced is different for each IOL manufacturer. The IOL of each manufacturer is designed so as to reduce a specific amount (value) of the spherical aberration of the cornea. In designing the aspheric IOL, a cornea model having a spherical aberration value that is the same as the specific amount of the spherical aberration to be reduced is set in advance, and the specific amount of the spherical aberration to be reduced by the aspheric IOL is determined by selecting optical parameters of the cornea model. In such an optical designing operation, the total spherical aberration of an optical system including a predetermined cornea model that has been set in advance and the designed aspheric IOL is zero (i.e., there is no spherical aberration).

The spherical aberration value of the predetermined cornea model is determined as follows. It is assumed that the spherical aberration value of the predetermined cornea model used when optically designing the aspheric IOL, and the average value of spherical aberrations for a population of eye patients being implanted with the IOL is the same. Alternatively, the spherical aberration value of the predetermined cornea model is determined by setting a spherical aberration value that partially reduces the cornea spherical aberration of the population of the eye patients.

The reference aspheric power is a power distribution of the aspheric IOL. The power distribution has a power distribution characteristic of being able to completely or partially reduce the average spherical aberration of the corneas (total cornea optical parameter) a population of aphakic patients. In the present specification, the spherical aberration value of the predetermined cornea model is 0.16 µm. FIG. 2 is also an example of the power distribution of an aspheric IOL that can completely reduce the spherical aberration of a cornea model having a spherical aberration value of 0.16 µm.

The first region is a region for correcting the visual acuity for far vision or the visual acuity for vision between far vision and intermediate vision.

The second region is a region for correcting the visual acuity for intermediate vision or the visual acuity for near vision.

The third region is a region for correcting the visual acuity for far vision.

As shown in FIG. 2, for the intraocular lens according to Embodiment 1 (and other aspects described in the present specification), the position r1 of the first boundary is set to 1.2 mm, and the position r2 of the second boundary is set to 1.6 mm. However, the values of r1 and r2 are not limited thereto. For example, r1 and r2 may be set such that 0.7 mm≤r1≤1.3 mm, and 1.1 mm≤r2≤2.0 mm. However, the values of r1 and r2 directly affect the areas of the first region, the second region, and the third region. Since the sizes of the first region, the second region, and the third region are determined according to the wearer, the values of r1 and r2 are not particularly limited.

The area ratio between the first region and the second region in a plan view may be set to be from 25:75 to 75:25, and the area ratio between the second region and the third region in a plan view may be set to be from 30:70 to 5:95.

As shown in FIG. 2, in the case of the first region, the lens center O has a base power, whereas the power increases as the distance from the lens center O increases. As a result, the visual acuity for far vision or the visual acuity for vision between far vision and intermediate vision is corrected in the first region.

<Condition a>

Preferably, the change in power is discontinuous on the first boundary and the second boundary. In that case, a base difference value resulting from subtracting the base power from a power $P_{B1Low}$ of the first region on the first boundary is preferably less than 50% of a base difference value resulting from subtracting the base power from a power $P_{B1High}$ of the second region on the first boundary. When the former base difference value is less than 50% of the latter, the function for correcting the visual acuity for far vision will not be compromised. It is preferable that, in an area from the lens center O to the first boundary, the power of the first region is continuously increased radially.

The expression "change in power is discontinuous" refers to, as its wording indicates, a case where a change in power when the distance from the lens center O increases is actually discontinuous in a plot in the form shown in FIG. 2, and also, when the plot is functionalized, the change in power when the distance from the lens center O increases is continuous but is steep, and thus is substantially discontinuous. Conversely, the expression "change in power is continuous" refers to a state that does not correspond to "change in power is not discontinuous".

As for determination of whether or not a change in power is "steep", a change in power is regarded as being steep when the change has a degree of change of 100 D/mm or more, for example. That is, even if a power discontinuously increases for every 0.01 mm away from a point located at a predetermined distance from the lens center O, the change in power is regarded as being steep if the change has a degree of change of 100 D/mm or more in an area within 0.05 mm from the point.

<Condition b>

The average value of the base difference values within the first region from the lens center O to the position r1 of the first boundary is preferably greater than 5 times the average value of the base difference values within the first region from a lens center O of a virtual spherical lens having a base power at the lens center O to the position r1. The former average value is preferably greater than or equal to 8 times, and more preferably greater than or equal to 10 times the latter average value. By satisfying this condition, it is possible to preferably correct the visual acuity for far vision or the visual acuity for vision between far vision and intermediate vision.

Note that the "base difference value on the first boundary" and the "average value of the base difference values" as described in the present specification are values exceeding 0 D.

<Condition c>

In the second region, the visual acuity when viewing an object at one intermediate vision distance or one near vision distance is corrected. Preferably, the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by the cornea. Cases where there are a plurality of positive constant powers will be described in the section of Modifications. In the present specification, a power resulting from addition of one positive constant power is mainly described, and the expression "one or more" may be omitted in that case.

As shown in FIG. 2, it is preferable that the power plot of the second region in Embodiment 1 has a shape resulting from shifting the plot of the reference aspheric power upward by the above-described constant value (the arrow A in FIG. 2). Accordingly, it is preferable that the power continuously decreases radially in the second region.

<Condition d>

The third region is a region for correcting the visual acuity for far vision. It is preferable that the power is reduced in the third region so as to provide a negative longitudinal spherical aberration that cancels at least part of a positive longitudinal spherical aberration caused by the cornea. Specifically, it is preferable that, as the distance from the lens center O increases, the power is decreased so as to cancel at least part (preferably greater than or equal to 70%, and more preferably the whole) of a positive longitudinal spherical aberration caused by the positive refractive power provided by the cornea. At that time, the power in the third region is preferably smaller than the base power.

In Embodiment 1, in an area from the position r2 of the second boundary to the position r3 of the outermost edge of the third region as viewed from the lens center O in the radial direction, the intraocular lens is set so as to have a power equal to a reference aspheric power, from the position r2 to the position r3, of a virtual aspheric lens that has a base power at the lens center O, and that cancels the whole of a positive longitudinal spherical aberration caused by the cornea. In view of this setting, it is preferable that the power continuously decreases radially in the third region.

Meanwhile, based on that the base power corresponds to correction for far vision, that the power in the third region is smaller than the base power, the description "visual acuity when viewing an object at one intermediate vision distance or one near vision distance is corrected" in <Condition c> above, and the above description of a power equal to a reference aspheric power, the following definitions can be derived.

<Condition e>

A power $P_{B2High}$ of the second region on the second boundary is greater than the base power, and a power $P_{B2Low}$ of the third region on the second boundary is smaller than the base power.

<Condition f>

In <Condition a> above, it is stated that it is preferable that the change in power is discontinuous on the first boundary and the second boundary. In addition, it is preferable that a second step value constituted by a value resulting from subtracting the power $P_{B2Low}$ of the third region from the power $P_{B2High}$ of the second region on the second boundary is greater than a first step value constituted by a value resulting from subtracting the power $P_{B1Low}$ of the first region from the power $P_{B1High}$ of the second region on the first boundary.

With the intraocular lens that satisfies the above-described conditions, the following effects can be achieved.

(Total Power)

Figure 3:
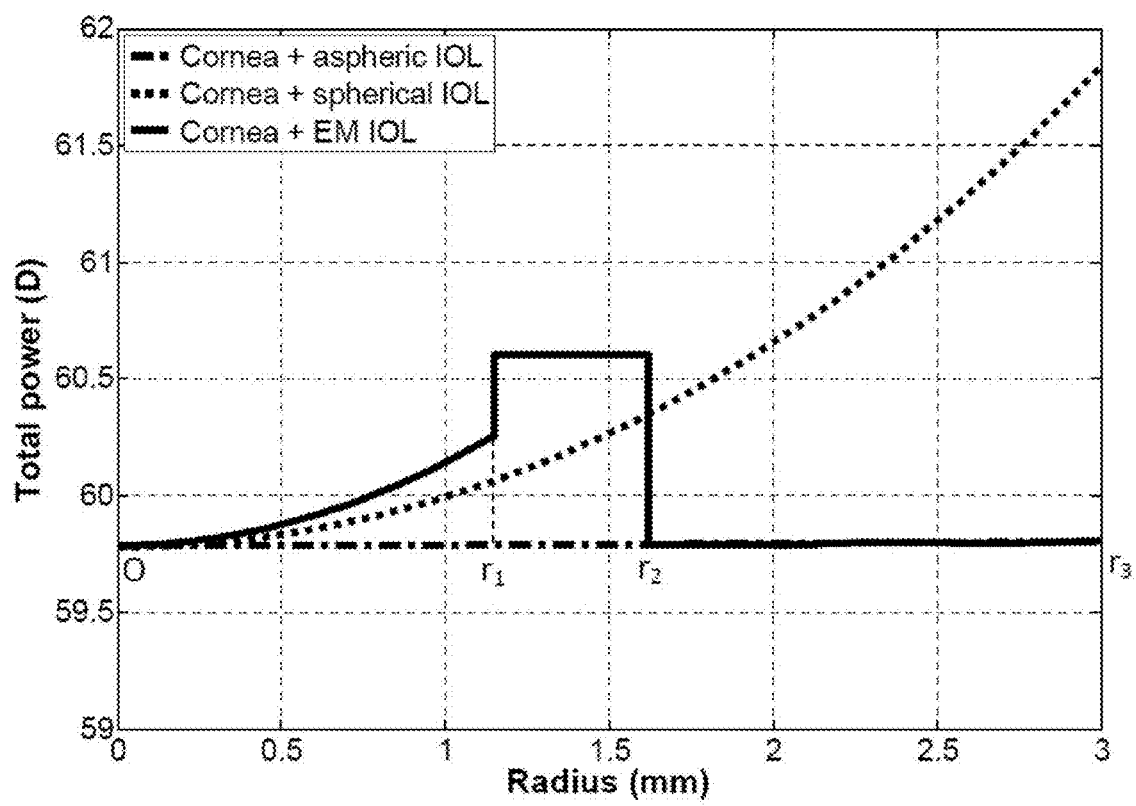
FIG. 3 is a plot showing a total power T (vertical axis) obtained by summing up the refractive power of a cornea and the power of the intraocular lens, versus a distance (horizontal axis) from the lens center O.

FIG. 3 is a plot showing a total power T (vertical axis) obtained by summing up the refractive power of a cornea and the power of the intraocular lens, versus a distance (horizontal axis) from the lens center O.

The conditions used in the plot shown in FIG. 3 are as follows.

Power of intraocular lens: 20.0 D
Position (r1) of first boundary: 1.15 mm
Position (r2) of second boundary: 1.62 mm
Positive constant power A added to reference aspheric power: approximately 1.15 D Examples of the cornea parameters are as shown below.
Radius of curvature of cornea anterior surface: 7.8 mm
Radius of curvature of cornea posterior surface: 6.5 mm
Conic constant of cornea anterior surface: −0.225
Conic constant of cornea posterior surface: 0
Distance (cornea thickness at cornea center) from cornea anterior surface to cornea posterior surface: 0.55 mm
Refractive index of material (cornea material) located between cornea anterior surface and cornea posterior surface: 1.3771
Distance (distance from center of cornea posterior surface to center of optical axis of anterior surface of intraocular lens) from cornea posterior surface to anterior surface of intraocular lens: 4.07 mm
Refractive index of material (aqueous humor) located between cornea posterior surface and anterior surface of intraocular lens: 1.336

The graph (plot) shown in FIG. 3 is obtained through optical calculation of an optical system including a cornea model and a designed enhanced monofocal intraocular lens (Enhanced monofocal IOL: referred as EM IOL). Although the details will be described later, an enhanced monofocal intraocular lens in which one or more positive constant powers of 1.25 D or more are added is referred to as EM IOL in the present specification. The EM IOL according to the present example is designed by modeling an optical system including a cornea and an IOL, and designing an aspheric anterior surface of the IOL, using a widely known optical design software ZEMAX (registered trademark) (manufactured by ZEMAX Development Corporation in the US).

As shown in FIG. 3, the total power T obtained by summing up the refractive power of the cornea and the power of the intraocular lens continuously increases in an area from the lens center O to the position r1 of the first boundary. Also, in an area from the position r1 of the first boundary to the position r2 of the second boundary, the total power T is constituted by one or more constant values. With the total power T, the visual acuity when viewing an object at one or more distances from an intermediate vision distance to a near vision distance is corrected. Also, in an area from the position r2 of the second boundary to the position r3 of the outermost edge of the lens body, the total power T is equal to a total power To obtained by summing up the refractive power of the cornea and the base power.

In other words, the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by the cornea.

It has also become clear that a good visual field can be effortlessly obtained according to the pupil diameter of the wearer.

(For Aperture Diameter of 2.5 mm or Less)

Figure 4A:
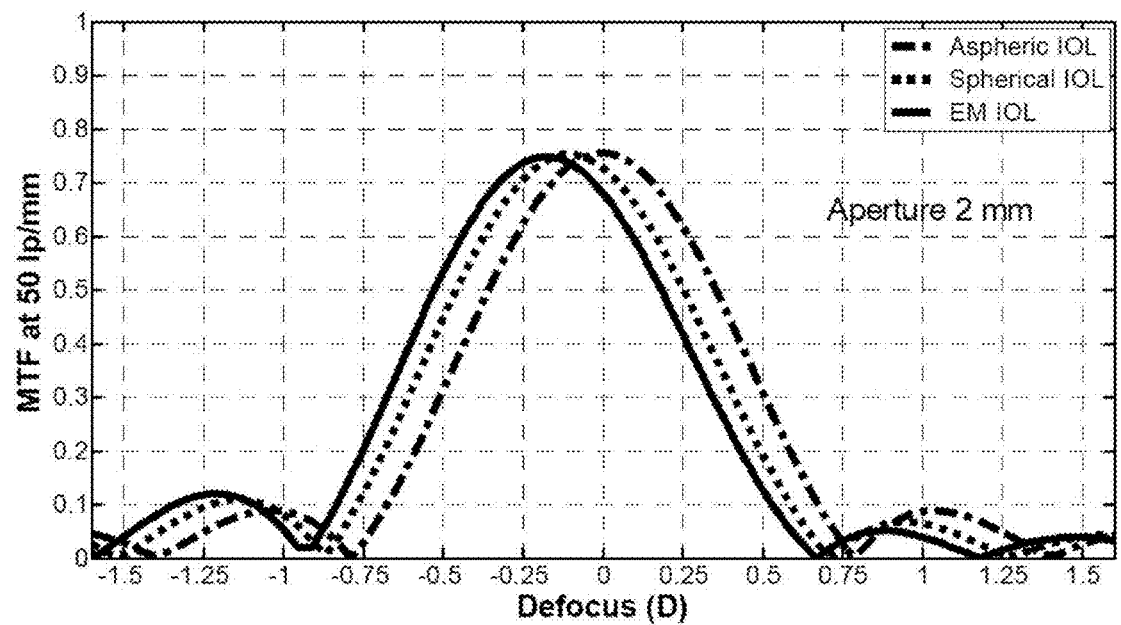
FIG. 4A is a plot showing an MTF value (vertical axis) indicating a contrast, versus a defocus value (horizontal axis) when the aperture diameter (pupil diameter) is set to 2 mm.

FIG. 4A is a plot showing an MTF value (vertical axis) indicating a contrast, versus a defocus value (horizontal axis) when the aperture diameter (pupil diameter) is set to 2 mm. This plot is also obtained using the above-described ZEMAX. As for specific details of the test, WO 2008/078804 filed by the Applicant may be used as the information.

Figure 7A:
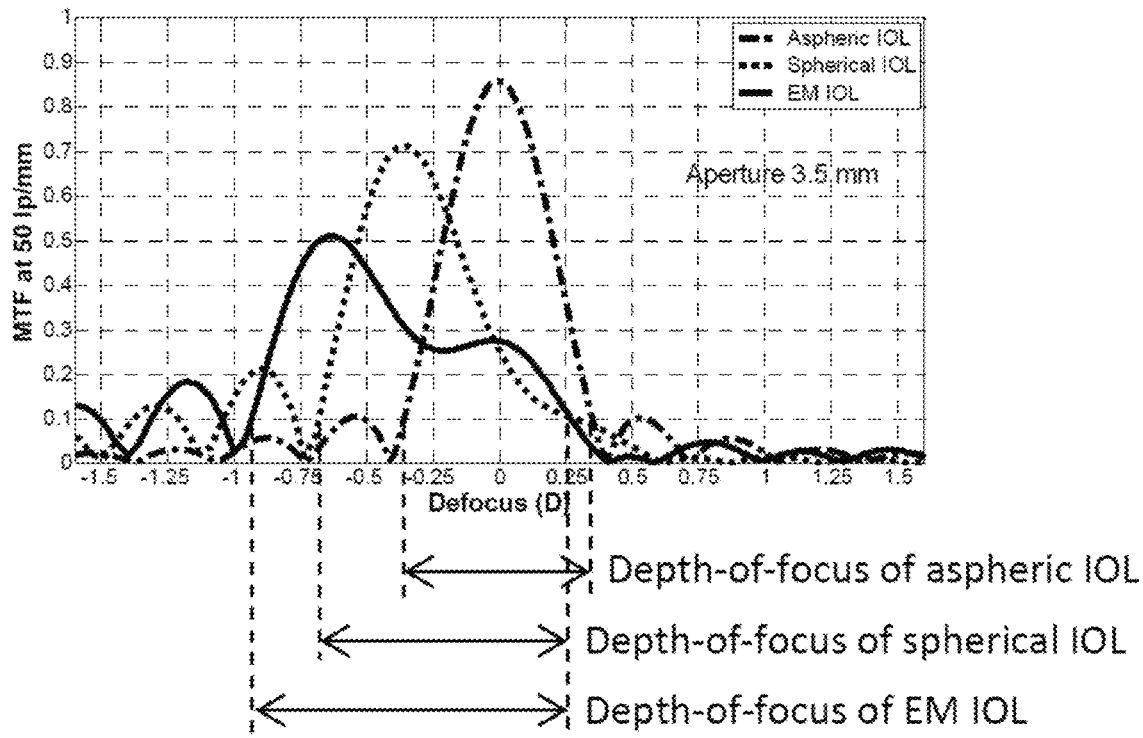
FIG. 7A is a plot showing an MTF value (vertical axis) indicating a contrast, versus a defocus value (horizontal axis) when the aperture diameter (pupil diameter) is set to 3.5 mm.

An MTF (Modulation Transfer Function) value is one of measures for evaluating the lens performance, and represents, as a spatial frequency characteristic, how faithfully a contrast that an object to be visually perceived has can be reproduced on an image plane. A high MTF value means that a contrast that is visually perceived by the wearer when viewing the object through the lens is high. In Embodiment 1 (and other aspects described in the specification), an MTF value when a spatial frequency of 50 line pairs/mm is chosen. In addition, the MTF value is set to 0.1 or more as this value is considered to provide a good visual field, and a maximum width (unit: diopter, D) of a region in which the MTF value is 0.1 or more is referred to as a depth of focus. An example of the width of the depth of focus is illustrated in FIG. 7A, which will be described later.

As shown in FIG. 4A, for a small (e.g., 2 mm) aperture diameter (pupil diameter), the EM IOL mainly function for correcting far vision. For example, in an outside environment under bright light, the pupil diameter decreases in order to control the amount of light to be refracted to the retina. In this this state (an outside environment under bright light), far vision is usually dominant. In the case of this state, the depth of focus of the intraocular lens according to Embodiment 1 is substantially the same as or slightly deeper than that of the virtual spherical lens as a result of being implanted with the intraocular lens according to Embodiment 1. The expression "substantially the same" refers to a case where the absolute value of difference in depth of focus between the intraocular lens according to the present invention and the virtual spherical lens is 0.25 D or less, and/or the difference in depth of focus between the two lenses is within 15% (the depth of focus of one of the lenses has a value equal to 85 to 115% of the depth of focus of the other).

Referring to FIG. 4A, the width, or in other words, the depth of focus, of the region of the plot (solid line) of the intraocular lens according to Embodiment 1 in which the MTF value is 0.1 or more is substantially the same as or slightly deeper than those of the plot (dotted line) of the virtual spherical lens and the plot (dashed dotted line) of the virtual aspheric lens. This means that, to a certain degree, a good visual field can be effortlessly obtained.

Figure 4B:
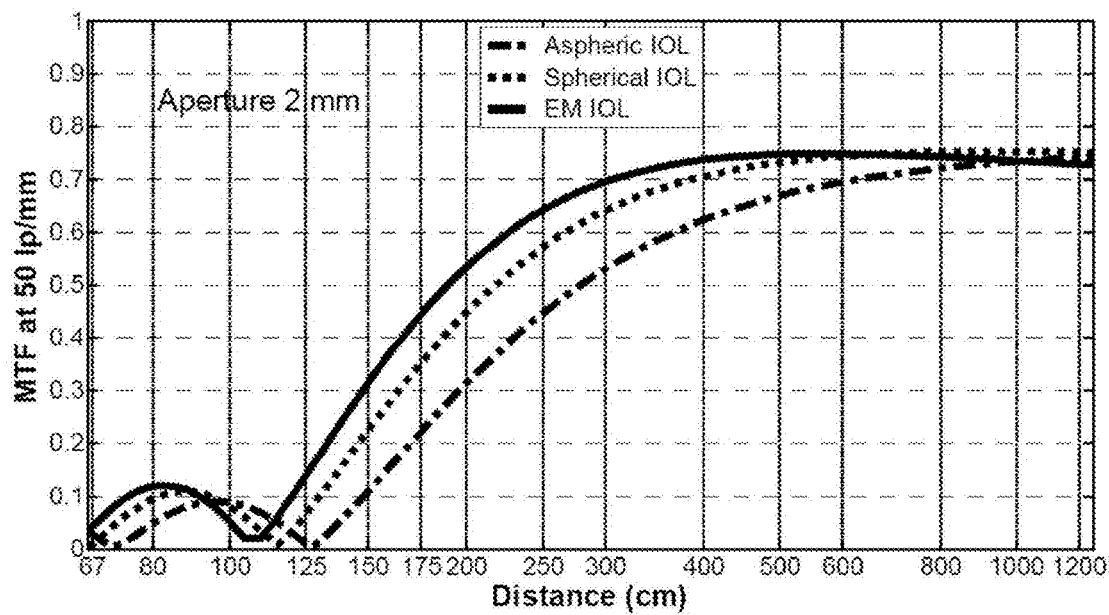
FIG. 4B is a plot showing an MTF value (vertical axis) indicating a contrast, versus an object distance (horizontal axis) from a corneal vertex when the aperture diameter (pupil diameter) is set to 2 mm.

FIG. 4B is a plot showing an MTF value (vertical axis) indicating a contrast, versus an object distance (horizontal axis) from a corneal vertex when the aperture diameter (pupil diameter) is set to 2 mm.

Referring to FIG. 4B, a position of the plot (solid line) of the intraocular lens according to Embodiment 1 at which the MTF value reaches 0.1 or more is located on the near side relative to the corresponding positions of the plot (dotted line) of the virtual spherical lens and the plot (dashed dotted line) of the virtual aspheric lens. For example, this position is nearer than 125 cm. This means that an object can be favorably perceived from the nearer side than in the cases of the virtual spherical lens and the virtual aspheric lens.

The relationships described in FIGS. 4A and 4B are the same in the following drawings, which show examples in which the aperture diameter is changed, and redundant portions of the descriptions about the plots have been omitted.

Figure 5A:
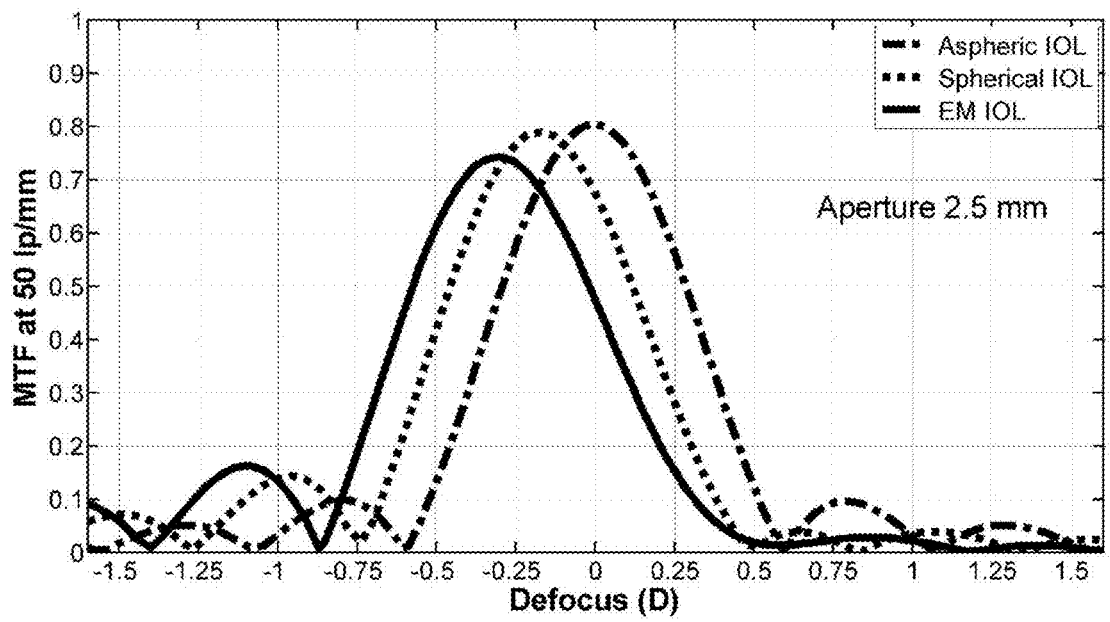
FIG. 5A is a plot showing an MTF value (vertical axis) indicating a contrast, versus a defocus value (horizontal axis) when the aperture diameter (pupil diameter) is set to 2.5 mm.

FIG. 5A is a plot showing an MTF value (vertical axis) indicating a contrast, versus a defocus value (horizontal axis) when the aperture diameter (pupil diameter) is set to 2.5 mm.

Figure 5B:
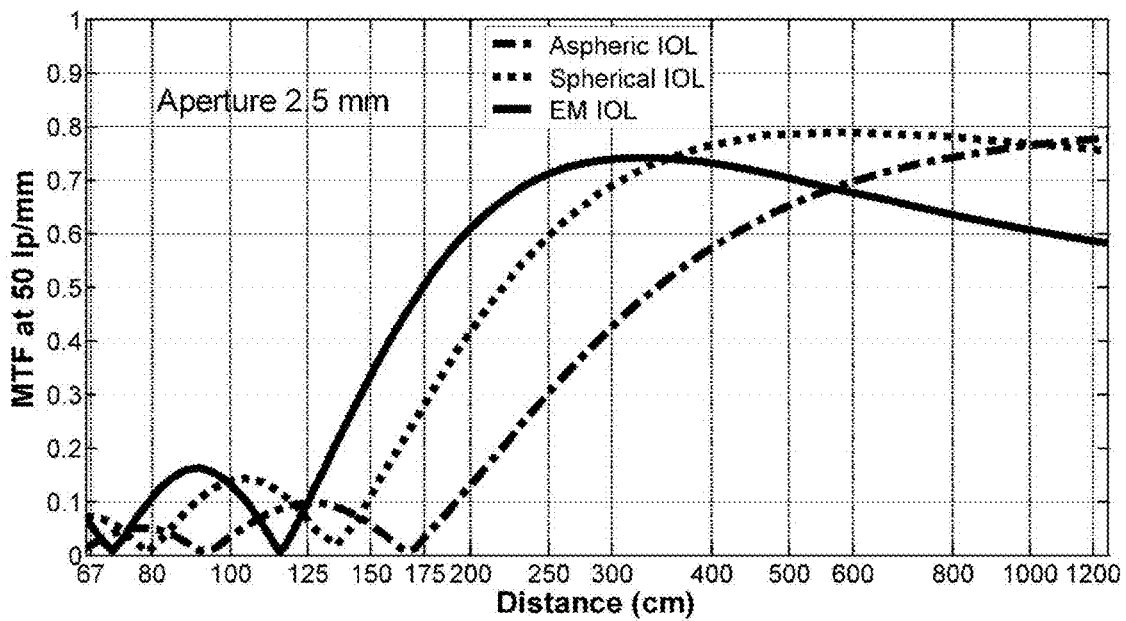
FIG. 5B is a plot showing an MTF value (vertical axis) indicating a contrast, versus an object distance (horizontal axis) from the corneal vertex when the aperture diameter (pupil diameter) is set to 2.5 mm.

FIG. 5B is a plot showing an MTF value (vertical axis) indicating a contrast, versus an object distance (horizontal axis) from the corneal vertex when the aperture diameter (pupil diameter) is set to 2.5 mm.

As compared with FIG. 4A, the graph of the EM IOL shown in FIG. 5A is displaced leftward (i.e., displaced to a near distance). This means that, for a pupil diameter of 2.5 mm, the MTF for intermediate vision slightly increases although the MTF (contrast) for far vision slightly decreases.

In the case of this state, as shown in FIG. 5A, the depth of focus is deeper than that of the virtual spherical lens as a result of being implanted with the intraocular lens according to Embodiment 1.

As shown in FIG. 5B, the position at which the MTF value reaches 0.1 or more is located on the near side relative to the corresponding positions of the plot (dotted line) of the virtual spherical lens and the plot (dashed dotted line) of the virtual aspheric lens. For example, this position is nearer than 125 cm. This means that an object can be favorably perceived from the nearer side than in the cases of the virtual spherical lens and the virtual aspheric lens.

(For Aperture Diameter of 3 mm to 4 mm)

Figure 6A:
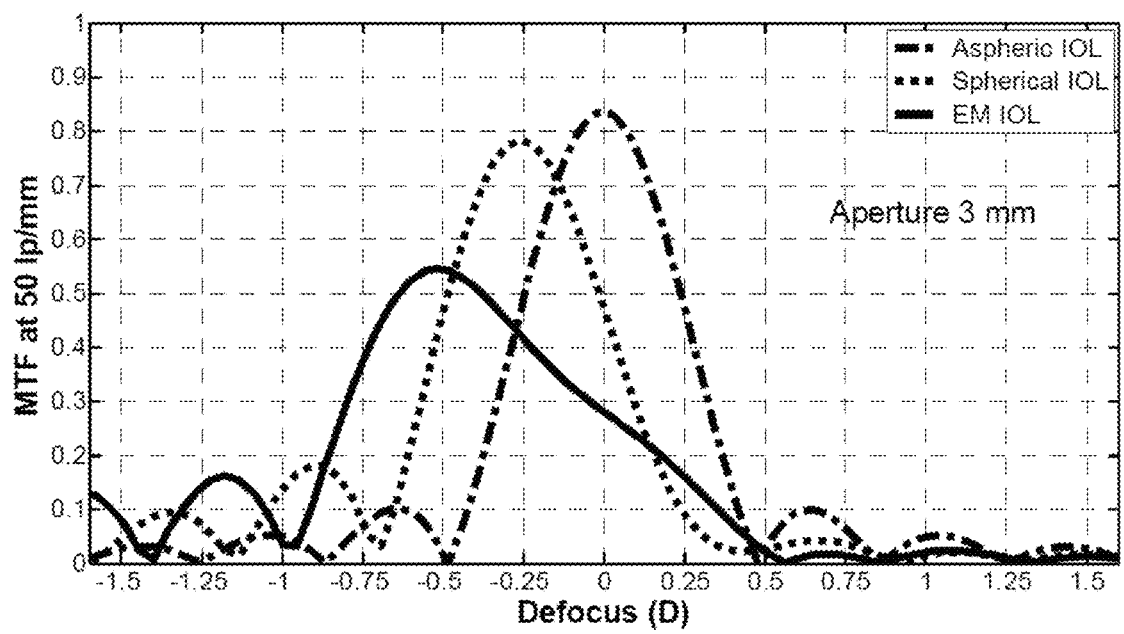
FIG. 6A is a plot showing an MTF value (vertical axis) indicating a contrast, versus a defocus value (horizontal axis) when the aperture diameter (pupil diameter) is set to 3 mm.

FIG. 6A is a plot showing an MTF value (vertical axis) indicating a contrast, versus a defocus value (horizontal axis) when the aperture diameter (pupil diameter) is set to 3 mm.

Figure 6B:
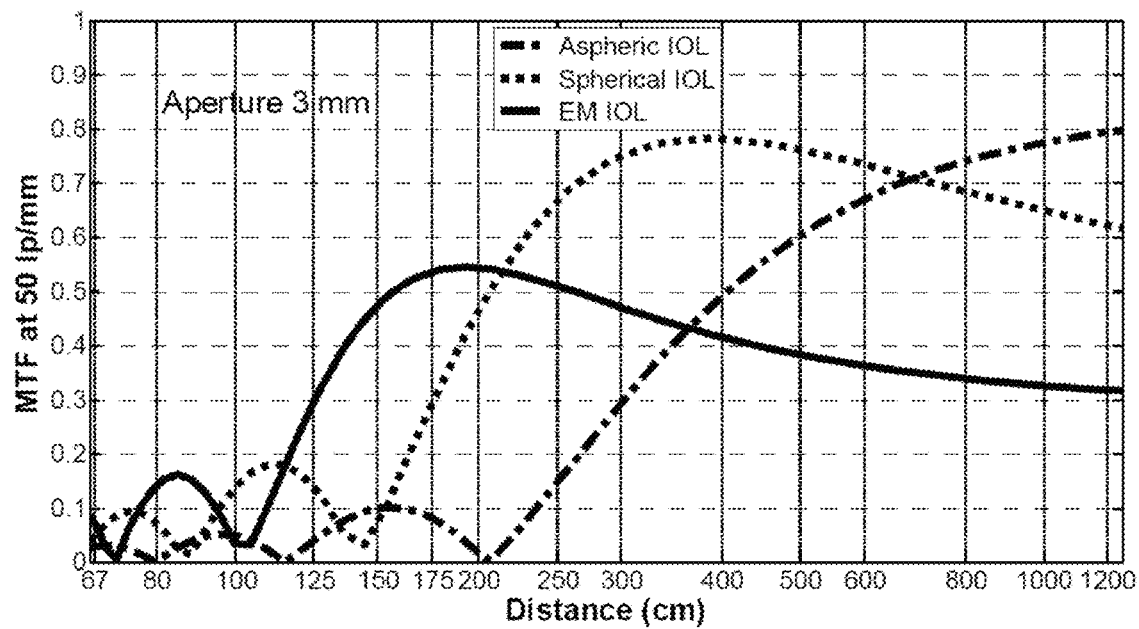
FIG. 6B is a plot showing an MTF value (vertical axis) indicating a contrast, versus an object distance (horizontal axis) from the corneal vertex when the aperture diameter (pupil diameter) is set to 3 mm.

FIG. 6B is a plot showing an MTF value (vertical axis) indicating a contrast, versus an object distance (horizontal axis) from the corneal vertex when the aperture diameter (pupil diameter) is set to 3 mm.

FIG. 7A is a plot showing an MTF value (vertical axis) indicating a contrast, versus a defocus value (horizontal axis) when the aperture diameter (pupil diameter) is set to 3.5 mm.

Figure 7B:
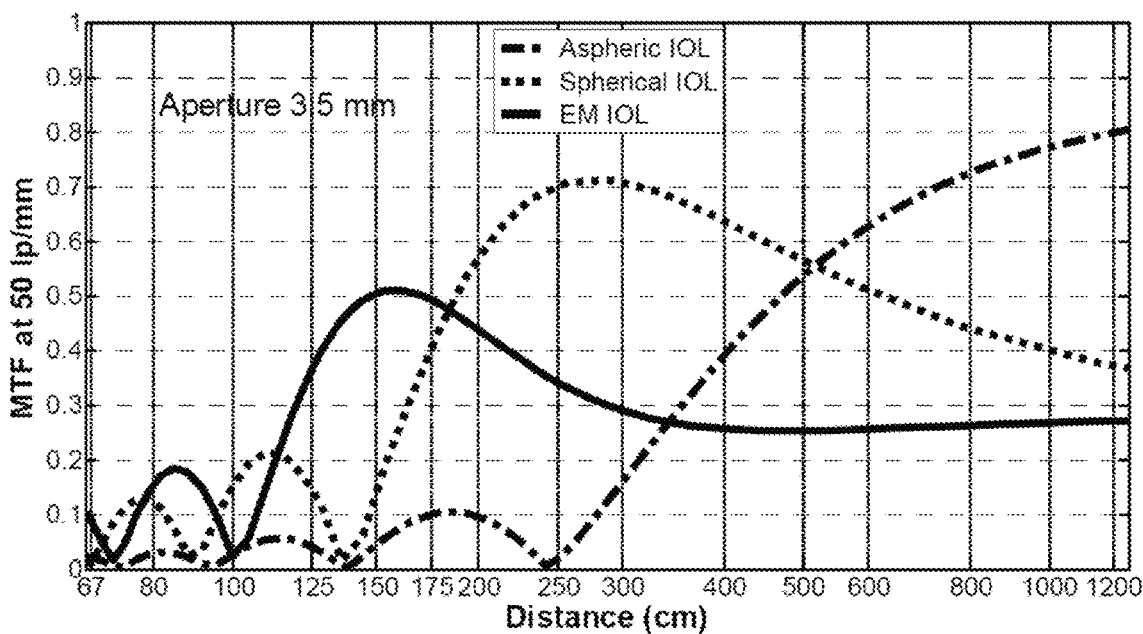
FIG. 7B is a plot showing an MTF value (vertical axis) indicating a contrast, versus an object distance (horizontal axis) from the corneal vertex when the aperture diameter (pupil diameter) is set to 3.5 mm.

FIG. 7B is a plot showing an MTF value (vertical axis) indicating a contrast, versus an object distance (horizontal axis) from the corneal vertex when the aperture diameter (pupil diameter) is set to 3.5 mm.

Figure 8A:
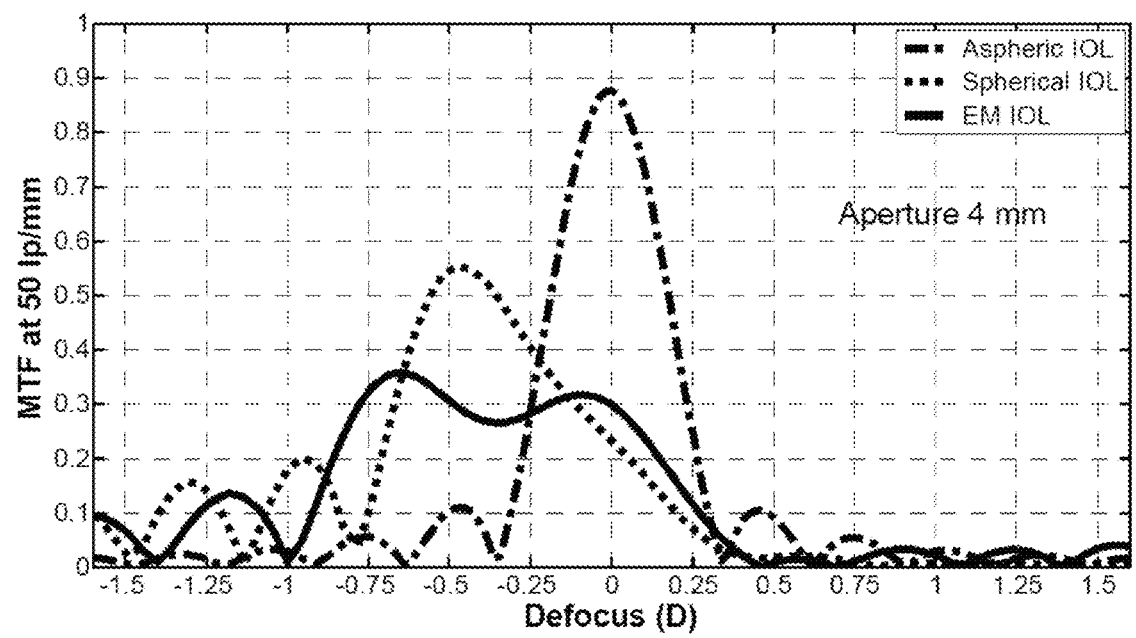
FIG. 8A is a plot showing an MTF value (vertical axis) indicating a contrast, versus a defocus value (horizontal axis) when the aperture diameter (pupil diameter) is set to 4 mm.

FIG. 8A is a plot showing an MTF value (vertical axis) indicating a contrast, versus a defocus value (horizontal axis) when the aperture diameter (pupil diameter) is set to 4 mm.

Figure 8B:
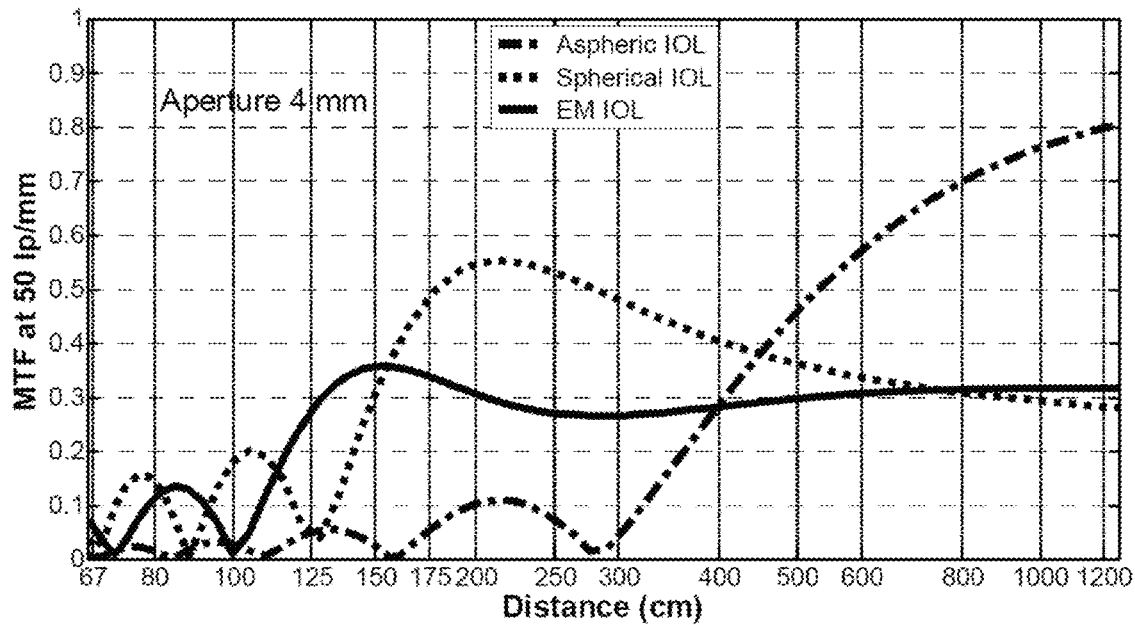
FIG. 8B is a plot showing an MTF value (vertical axis) indicating a contrast, versus an object distance (horizontal axis) from the corneal vertex when the aperture diameter (pupil diameter) is set to 4 mm.

FIG. 8B is a plot showing an MTF value (vertical axis) indicating a contrast, versus an object distance (horizontal axis) from the corneal vertex when the aperture diameter (pupil diameter) is set to 4 mm.

As shown in FIGS. 6A to 8A, for a medium (e.g., 3 to 4 mm) pupil diameter, the peak of the graph of the defocus-MTF value is lower than that for a small pupil diameter (<2.5 mm), but the visual acuity for intermediate vision is improved (i.e., the MTF value for intermediate vision increases).

In the case of this state, as shown in FIGS. 6A to 8A, the depth of focus is deeper than that of the virtual spherical lens as a result of being implanted with the intraocular lens according to Embodiment 1, as in the case of an aperture diameter of 2.5 mm or less. As shown in FIGS. 6B to 8B, the position at which the MTF value reaches 0.1 or more is located on the near side relative to the corresponding positions of the plot (dotted line) of the virtual spherical lens and the plot (dashed dotted line) of the virtual aspheric lens. For example, this position is nearer than 125 cm. This means that an object can be favorably perceived from the nearer side than in the cases of the virtual spherical lens and the virtual aspheric lens.

In the case of being implanted with the intraocular lens according to Embodiment 1, the contrast peak value is lowered as compared with that of the virtual aspheric lens. On the other hand, when the MTF value is above a certain level, the difference in vision is not significantly perceived by the wearer even if the MTF value varies. With the focus on this point, the present inventor has arrived at a configuration of an intraocular lens with which an object can be favorably perceived at the nearer side than in the cases of the virtual spherical lens and the virtual aspheric lens, while the depth of focus, which is the width of the region in which the MTF value is 0.1 or more, is widened even if the contrast peak value is lowered.

(For Aperture Diameter of 5 mm or More)

Figure 9A:
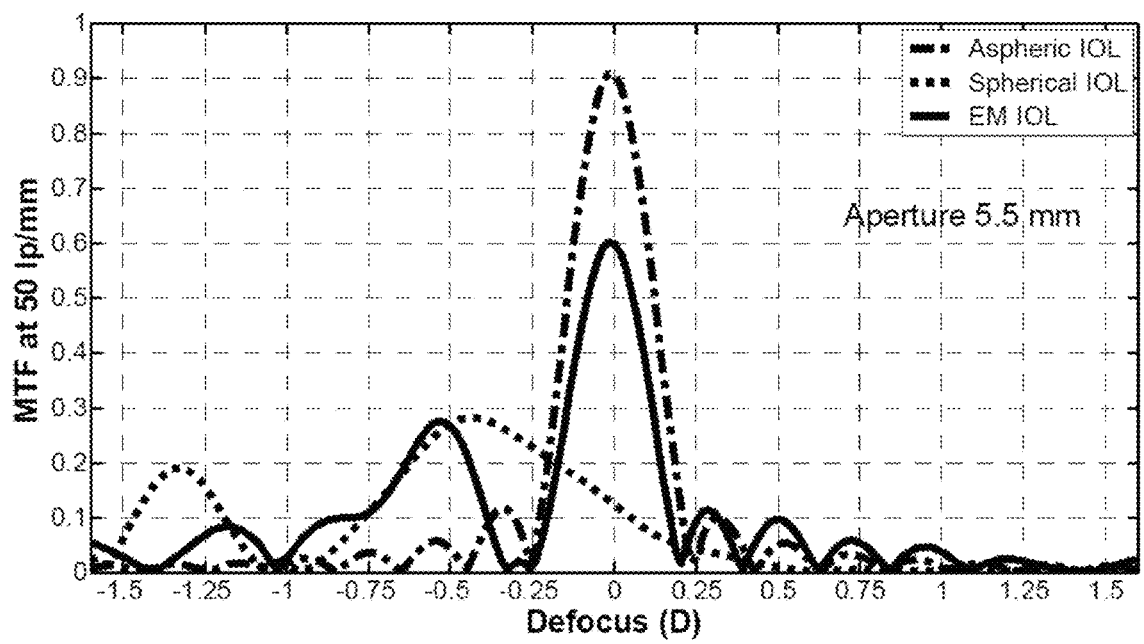
FIG. 9A is a plot showing an MTF value (vertical axis) indicating a contrast, versus a defocus value (horizontal axis) when the aperture diameter (pupil diameter) is set to 5.5 mm.

FIG. 9A is a plot showing an MTF value (vertical axis) indicating a contrast, versus a defocus value (horizontal axis) when the aperture diameter (pupil diameter) is set to 5.5 mm.

Figure 9B:
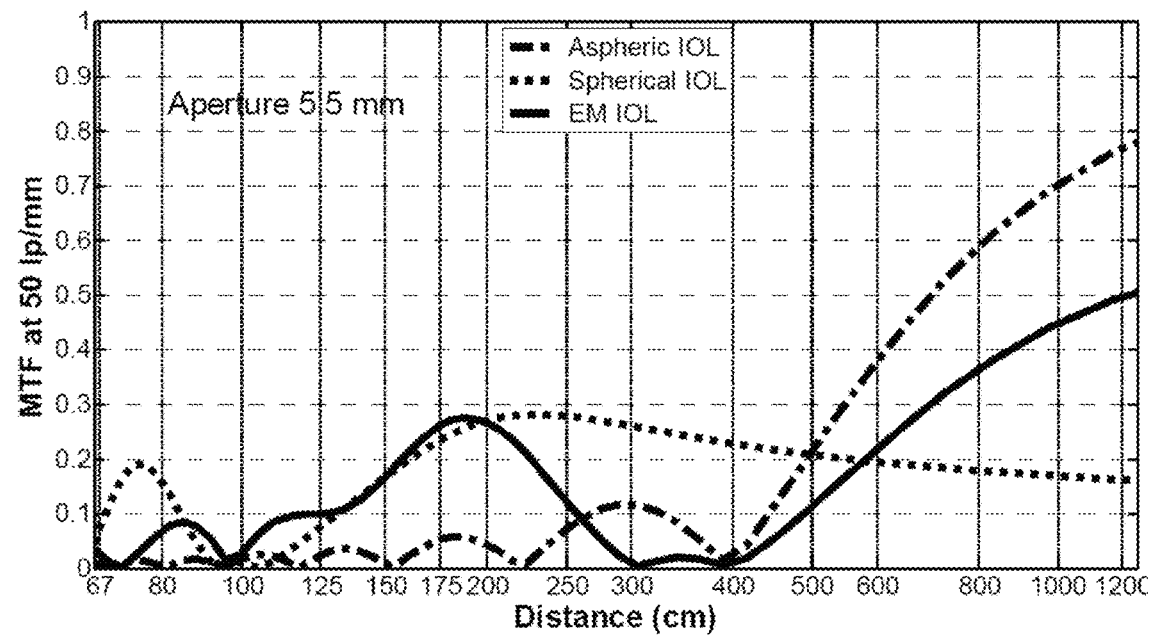
FIG. 9B is a plot showing an MTF value (vertical axis) indicating a contrast, versus an object distance (horizontal axis) from the corneal vertex when the aperture diameter (pupil diameter) is set to 5.5 mm.

FIG. 9B is a plot showing an MTF value (vertical axis) indicating a contrast, versus an object distance (horizontal axis) from the corneal vertex when the aperture diameter (pupil diameter) is set to 5.5 mm.

As shown in FIG. 9A, for a large (e.g., 5.5 mm) aperture diameter (pupil diameter), the EM IOL mainly function for correcting far vision. For example, in an outside environment at night (dark condition), the pupil diameter increases in order to refract a sufficient amount of light to the retina. In this state (in an outside environment at night), far vision is usually dominant. In the case of this state (i.e., a dark environment, for a large pupil diameter), as shown in FIG. 9A, a high MTF value can be obtained for far vision (in the vicinity of a defocus of 0 D) as a result of being implanted with the intraocular lens according to Embodiment 1, as in the case of the virtual aspheric lens.

The foregoing provides the description of Embodiment 1. Other embodiments and the like will be described below.

Note that the aspect of Embodiment 1 is applicable to other embodiments to the extent not inconsistent with the description of Embodiment 1.

Embodiment 2 is an aspect focusing on the total power T, from among the effects described in relation to Embodiment 1.

Embodiment 3 is an aspect focusing on the MTF value for each aperture diameter, from among the effects described in relation to Embodiment 1.

Embodiment 4 is an aspect that represents the sag value of the intraocular lens according to Embodiment 1 by one polynomial equation. A sag value is a vertical distance from a tangent plane at an optical center to an anterior surface of a virtual spherical lens.

Embodiment 2

In Embodiment 2, <Condition a>, <Condition b>, and <Condition e> described in Embodiment 1 are used. Again, it is a combination of the conditions that constitutes an aspect of the present invention, and the effects of the present invention are achieved thereby. The conditions are listed based on ease of description.

For an intraocular lens according to Embodiment 2, the following conditions are used based on FIG. 3.

<Condition g>

The first region, the second region, and the third region are shaped such that a total power T obtained by summing up a refractive power of the cornea and a power of the intraocular lens increases radially (preferably continuously) in an area from the lens center O to the position r1 of the first boundary, the total power T is equal to the total power To at the lens center O in an area from the position r2 of the second boundary to the position r3 of the outermost edge of the third region, and the total power T is equal to a value resulting from adding one or more positive constant powers to the total power To in area from the position r1 of the first boundary to the position r2 of the second boundary.

Using <Condition g> in addition to <Condition a> and <Condition b> can also provide the effects of the present invention, and can constitute an invention.

Embodiment 3

In Embodiment 3, <Condition a>, <Condition b>, and <Condition e> described in Embodiment 1 are used as in the case of Embodiment 2. Also, for an intraocular lens according to Embodiment 3, the following conditions are used based on FIGS. 4A to 9A.

<Condition h>

"The first region and the second region are sized such that, assuming that all light rays for a spatial frequency of 50 line pairs/mm pass through a virtual cornea and the intraocular lens, a depth of focus is substantially the same as or deeper than a depth of focus of the virtual spherical lens for an aperture diameter of 2.5 mm or less, a depth of focus is at least 10% deeper than the depth of focus of the virtual spherical lens for an aperture diameter of 3 to 4 mm, and a contrast peak is present at a defocus value in a range from −0.25 D to 0.25 D (e.g., at a defocus value of zero) for an aperture diameter of 5 mm or more."

The defocus values is plotted on the horizontal axis of a graph of a through focus MTF (=through focus response (TFR)).

Using only <Condition h> can also provide the effects of the present invention, and can constitute an invention.

Embodiment 4

In Embodiment 4, <Condition a>, <Condition b>, <Condition d>, and <Condition e> described in Embodiment 1 are used as in the case of Embodiment 2. In addition, for an intraocular lens according to Embodiment 4, the following conditions are used.
<Condition i>
A sag value of an anterior surface, a sag value of a posterior surface, or the sag values of both the anterior surface and the posterior surface of the intraocular lens are represented by the following polynomial equation:

$$z = \frac{cr^2}{1 + \sqrt{1 - (1+k)c^2 r^2}} + a_1 r^2 + a_2 r^4 + a_3 r^6 + a_4 r^8 + \ldots + a_n r^{2n} \quad \text{[Math. 5]}$$

z: sag value
c: curvature of lens center (=1/R[m])
k: conic constant
r: distance from lens center, i.e., radius
$a_1, a_2, \ldots, a_{n-1}, a_n$: coefficient
the power of each of the regions is represented by the following polynomial equation:

$$P_i = c_{0,i} + c_{1,i} r^1 + c_{2,i} r^2 + c_{3,i} r^3 + c_{4,i} r^4 + \ldots + c_{n,i} r^n \quad \text{[Math. 6]}$$

$P_i$: power of i-th region
r: distance from lens center, i.e., radius
$c_{0,i}, c_{1,i}, \ldots, c_{n-1,i}, c_{n,i}$: coefficient
the power of the second region is represented by the following equation:

$$P_2 = A + P_3 \quad \text{[Math. 7]}$$

$P_2$: power of second region
$P_3$: power of third region
A: addition power to reference aspheric power
A is a value obtained by subtracting, from the power of the second region at a predetermined position r2x within the second region, a reference aspheric power, at the position r2x, of a virtual aspheric lens that has a base power at a lens center O, and that cancels the whole of a positive longitudinal spherical aberration caused by the cornea, and
the power of the third region is represented by the following polynomial equation:

$$P_3 = c_{0,3} + c_{1,3} r^1 + c_{2,3} r^2 + c_{3,3} r^3 + c_{4,3} r^4 + \ldots + c_{n,3} r^n \quad \text{[Math. 8]}$$

$P_3$: power of third region
$c_{0,3}, c_{1,3}, \ldots, c_{n-1,3}, c_{n,3}$: coefficient
Using only <Condition i> can also provide the effects of the present invention, and can constitute an invention.

The intent of Embodiment 4 is to set a polynomial equation for determining a refractive power for each of the first region, the second region, and the third region, while representing the shape of the anterior surface of the lens body using a sag value, and defining the sag value using one polynomial equation. The sag value may also be represented by three polynomial equations. In the case of representing the sag value using three polynomial equations, a sag equation for each of the regions (the first region, the second region, and the third region) is represented by one polynomial equation.

Since the sag value is defined using one polynomial equation, strictly speaking, the power actually continuously changes on the first boundary and the second boundary. On the other hand, the change in power when the distance from the lens center O increases is continuous, but is steep. That is, a state in which the change in power is substantially discontinuous is defined using a sag value obtained using one polynomial equation.

Figure 10:
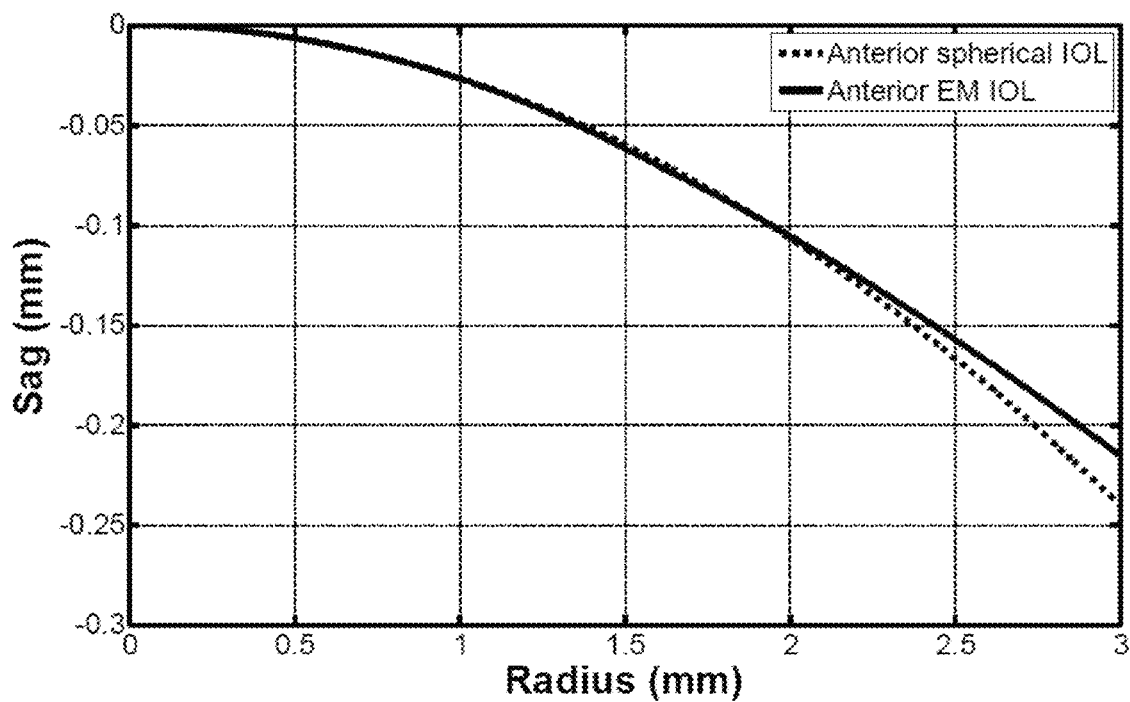
FIG. 10 is a plot showing a sag value (vertical axis) of an anterior surface of a lens body versus a distance (horizontal axis) from the lens center O.

FIG. 10 is a plot showing a sag value (vertical axis) of an anterior surface of a lens body versus a distance (horizontal axis) from the lens center O. That is, FIG. 10 is a plot of [Math. 6] above. When the sag value of one surface of the lens body is set as shown in FIG. 10, the other surface of the lens body may be spherical or toric. Ultimately, as long as the power plot shown in FIG. 2 can be realized while the sag value of one surface is set as shown in FIG. 10, the shape of the other side is not particularly limited.

In Embodiment 4, it is preferable that a total power T obtained by summing up the refractive power of the cornea and the power of the intraocular lens is constituted by one or more constant values in an area from the position r1 of the first boundary to the position r2 of the second boundary, and a visual acuity when viewing an object at one or more distances of an intermediate vision distance to a near vision distance is corrected by the total power T.

In Embodiment 4 (and Embodiment 3 above), it is preferable that the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by the cornea.

Modifications

The intraocular lens according to the present embodiment is not limited to the embodiments described above, and includes various changes and modifications as far as specific effects achieved by the constituent elements of the invention and combinations thereof can be derived.

A visual acuity correction region other than the first region, the second region, and the third region may be provided in a direction away from the lens center O relative to the outer edge of the third region, or in other words, the position r3.

Although a case where the lens body includes the first region, the second region, and the third region is described in each of the embodiments, the present invention is not limited thereto. For example, the lens body may include an optical part including the first region, the second region, and the third region, and a peripheral part that is disposed at an outer edge of the optical part so as to be connected to a supporting part, and that does not have a desired optical function. In this case, the position r3 of the outermost edge of the third region constitutes a boundary position with the peripheral part that does not have a desired optical function. In the case where the peripheral part is not provided, the outermost edge of the lens body constitutes the position r3.

Although a case where <Condition a> is satisfied for the first region is illustrated in each of the embodiments, the present invention is not limited thereto.

Figure 11:
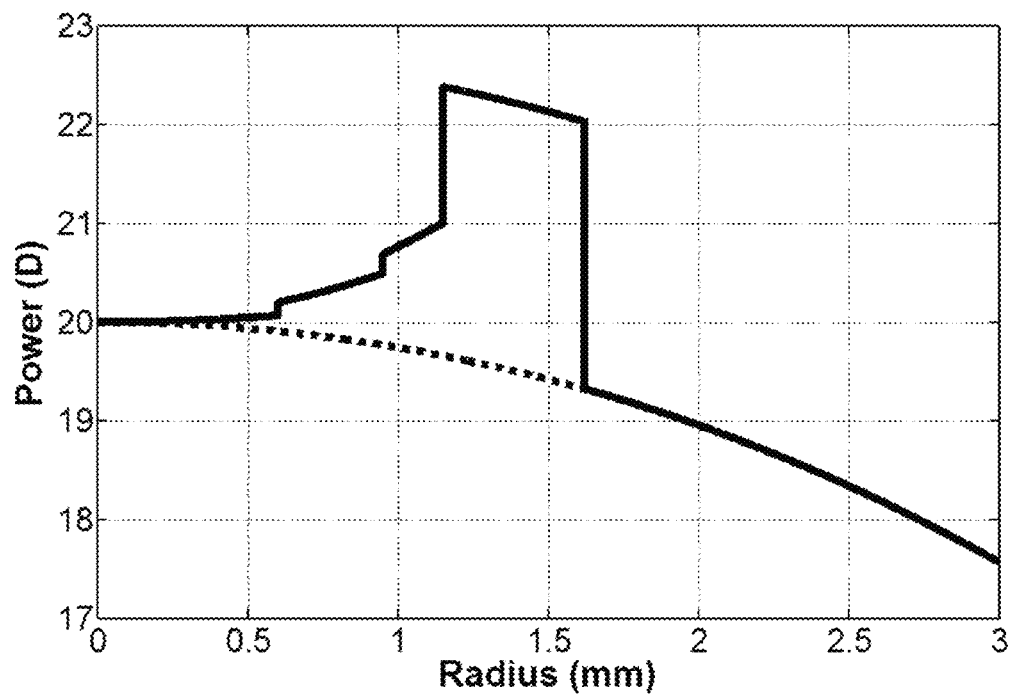
FIG. 11 is a plot (Modification 1) showing a refractive power (vertical axis) provided by the intraocular lens versus a distance (horizontal axis) from the lens center O.

FIG. 11 is a plot (Modification 1) showing a refractive power (vertical axis) provided by the intraocular lens versus a distance (horizontal axis) from the lens center O.

As shown in FIG. 11, in the first region, the power may not be significantly increased from the base power when the distance from the lens center O begins to increase, whereas the power may be discontinuously increased in a stepwise manner in the vicinity of the first boundary.

On the other hand, using this modification leads to introduction of a new design concept in the first region, thus complicating the design. Therefore, it is more preferable to satisfy <Condition a> because the design will not be complicated.

Figure 12:
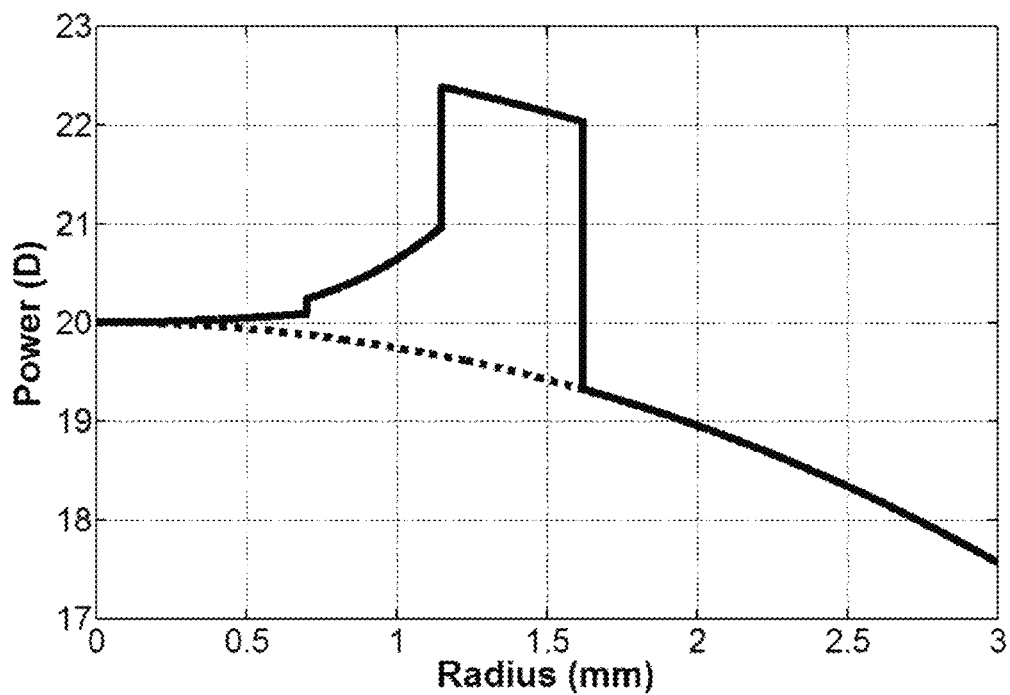
FIG. 12 is a plot (Modification 2) showing a refractive power (vertical axis) provided by the intraocular lens versus a distance (horizontal axis) from the lens center O.

FIG. 12 is a plot (Modification 2) showing a refractive power (vertical axis) provided by the intraocular lens versus a distance (horizontal axis) from the lens center O.

As shown in FIG. 12, in the first region, the power may be increased discontinuously when the distance from the lens center O begins to increase, and the power may be changed continuously in the vicinity of the first boundary.

On the other hand, using this modification leads to introduction of a new design concept in the first region, thus complicating the design. Therefore, it is more preferable to satisfy <Condition a> because the design will not be complicated.

Although a case where <Condition b> is satisfied for the first region is illustrated in each of the embodiments. Specifically, the condition is defined using the average value of the base difference values. On the other hand, an integral value within the first region of the base difference values from the lens center O to the position r1 of the first boundary may be used together with or in place of the average value. In the case of using the integral value as wall, the preferred examples of the numerical range thereof are the same as those for <Condition b>.

In Embodiment 1, a case where the visual acuity when viewing an object at one intermediate vision distance or one near vision distance is corrected in the second region is described. However, the present invention is not limited thereto.

Figure 13A:
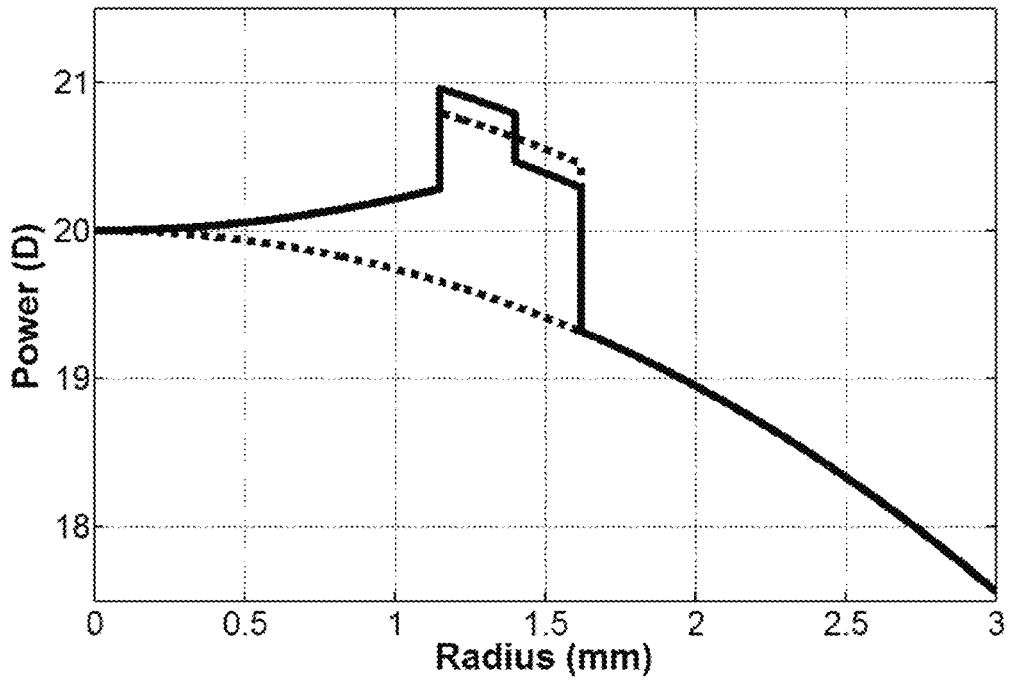
FIG. 13A is a plot (Modification 3-1) showing a refractive power (vertical axis) provided by the intraocular lens versus a distance (horizontal axis) from the lens center O.

FIG. 13A is a plot (Modification 3-1) showing a refractive power (vertical axis) provided by the intraocular lens versus a distance (horizontal axis) from the lens center O.

Figure 13B:
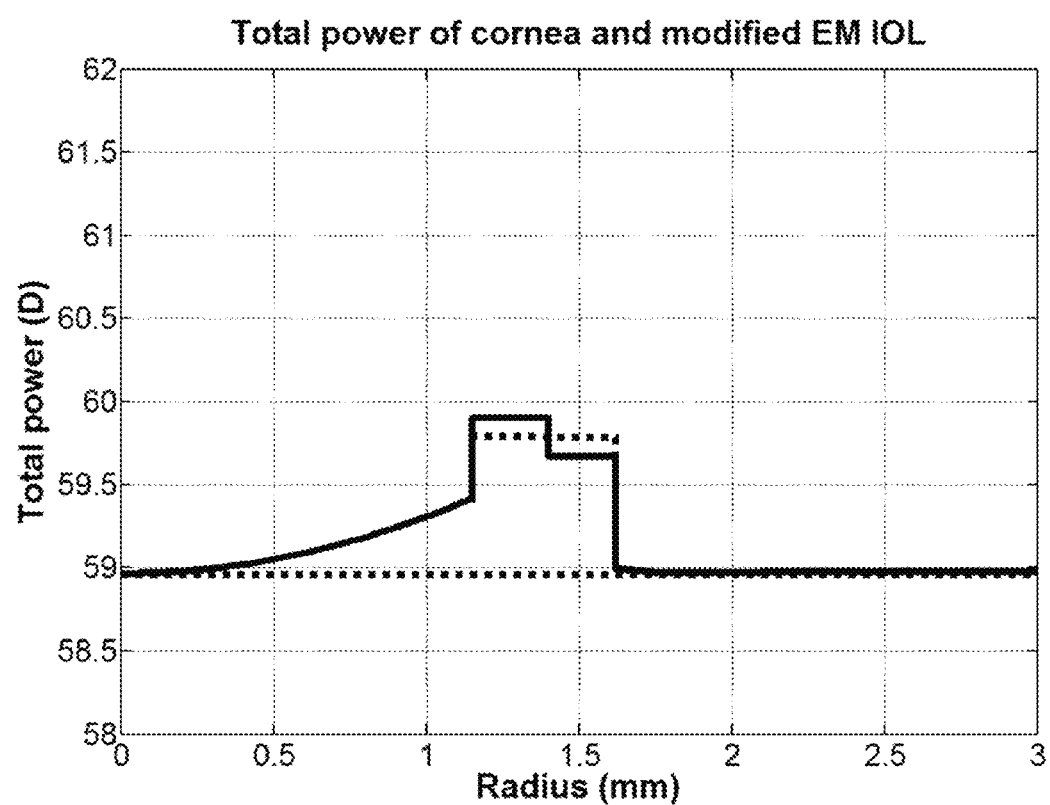
FIG. 13B is a plot (Modification 3-2) showing a total power T (vertical axis) obtained by summing up the refractive power of a cornea and the power of the intraocular lens, versus a distance (horizontal axis) from the lens center O.

FIG. 13B is a plot (Modification 3-2) showing a total power T (vertical axis) obtained by summing up the refractive power of a cornea and the power of the intraocular lens, versus a distance (horizontal axis) from the lens center O.

In FIGS. 13A and 13B, the power plot of the second region before modification is depicted by the broken line so as to show the states before and after modification.

As shown in FIGS. 13A and 13B, two intermediate vision distances or two near vision distances may be set in the second region. That is, although it is defined that "adding one or more positive constant powers to a reference aspheric power" in <Condition c> in Embodiment 1, two different such constant values may be set. The number of the types of constant values can be one to three, but is preferably one to two, and more preferably one, in order to prevent complication of the design. When there are a plurality of positive constant powers, a constant value added in an area of the second region that includes the position r1 is greater than a constant value added in an area that is adjacent to the aforementioned area and that is located away from the lens center O. When there are three or more different positive constant powers, a constant value added in the area located away is greater than a constant value added in an area that is adjacent to the area located away and that is located farther away from the lens center O. That is, it is preferable that, in the second region, the constant value added decreases as the distance from the lens center O increases.

In Embodiment 1, a case is illustrated where the third region is set so as have a power equal to a reference aspheric power, in an area from the position r2 to the position r3, of a virtual aspheric lens from the position r2 of the second boundary to the position r3 of the outermost edge of the third region. However, the present invention is not limited thereto. The third region need only be provided with a negative longitudinal spherical aberration that cancels at least part of a positive longitudinal spherical aberration caused by the cornea. However, a deviation from the plot of the reference aspheric power means generation of a longitudinal spherical aberration, and thus leads to insufficient correction of the visual acuity. Therefore, it is preferable to use the aspect described in Embodiment 1.

The term "a power equal to a reference aspheric power" indicates that, at a predetermined distance from the lens center O, the deviation from the reference aspheric power is less than ±0.30 D (preferably less than ±0.15 D). That is, the third region is a range from the position r2 to the position r3 in FIG. 2 described in Embodiment 1.

Similarly, the term "a power resulting from adding one or more positive constant powers to a reference aspheric power" in the second region indicates that, at a predetermined distance from the lens center O, the deviation from the reference aspheric power of a plot resulting from adding one or more positive constant powers to the reference aspheric power is less than ±0.30 D (preferably less than ±0.15 D). That is, the term indicates a radial region in which the above-described deviation is less than ±0.30 D. This range corresponds to a range from the position r1 to the position r2 in FIG. 2 described in Embodiment 1. Also, the first region can be defined as being inside the second region.

Taking the above-described modifications into account, <Condition e> may be deleted from Embodiment 1 to expand the technical scope thereof.

Although an intraocular lens is illustrated in each of the embodiments, the technical idea of the present invention is also applicable to a contact lens. When an expression encompassing a contact lens and an intraocular lens is defined as an ophthalmic lens, the term "intraocular lens" described in the present specification may be replaced by the term "ophthalmic lens".

Although an intraocular lens is illustrated in each of the embodiment, the technical idea of the present invention is also applicable to a designing method or a manufacturing method of an intraocular lens. For example, a designing method or a manufacturing method of the intraocular lens corresponding to Embodiment 1 is as follows.

"A designing method or a manufacturing method of an intraocular lens including at least three visual acuity correction regions that are concentric with a lens center O at which a predetermined base power is set, and that are adjacent to each other, the designing method or the manufacturing method including:

setting the visual acuity correction regions as a first region including the lens center O, and a second region and a third region disposed in this order radially from the first region, when r1 being a position of a first boundary between the first region and the second region, and r2 being a position of a second boundary between the second region and the third region, as viewed radially from the lens center O, the first region being a region for correcting a visual acuity for far vision or a visual acuity for vision between far vision and intermediate vision, the second region being a region for correcting a visual acuity for intermediate vision or a visual acuity for near vision, the third region being a region for correcting the visual acuity for far vision, a change in power being discontinuous on the first boundary and the second boundary, a base difference value (exceeding 0 D) obtained by subtracting the base power from a power $P_{B1Low}$ of the first region on the first boundary being less than 50% of a base difference value (exceeding 0 D) obtained by subtracting the base power from a power $P_{B1High}$ of the second region on the first boundary, an average value (exceeding 0 D) of the base difference values within the first region from the lens center O to the position r1 of the first boundary being greater than 5 times an average value (exceeding 0 D) of the base difference values within the first region from a lens center O of a virtual spherical lens having a base power at the lens center O to the position r1, the second region having a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by a cornea;

reducing the power in the third region so as to provide a negative longitudinal spherical aberration that cancels at least part of the positive longitudinal spherical aberration caused by the cornea, a second step value constituted by a value obtained by subtracting a power $P_{B2Low}$ of the third region from a power $P_{B2High}$ of the second region on the second boundary being greater than a first step value constituted by a value obtained by subtracting the power $P_{B1Low}$ of the first region from the power $P_{B1High}$ of the second region on the first boundary; and setting the power $P_{B2High}$ of the second region on the second boundary to be greater than the base power, and the power $P_{B2Low}$ of the third region on the second boundary to be less than the base power."

The wording of the intraocular lens according to each of the other embodiments can be similarly changed into a designing method or a manufacturing method of the intraocular lens.

The technical idea of the present invention is also applicable to a monofocal lens. Examples thereof include an enhanced monofocal intraocular lens (Enhanced monofocal IOL: referred as EM IOL) in which one or more positive constant powers of 1.25 D or less are added. The technical idea of the present invention is also applicable to a multifocal lens (e.g., in which one or more positive constant powers, i.e., addition powers of 2.5 D or greater are added), and is also applicable to an extended depth-of-focus intraocular lens (extended depth-of-focus IOL: commonly called EDOF), which is a lens in between these lenses (e.g., in which one or more positive constant powers of greater than 1.25 D and less than 2.5 D (e.g., 2 D) are added). The classification in the present paragraph is merely an example, and the present invention does not exclude, for example, a case where two types of positive constant powers are set, with one value being 1.25 D or less, and the other value being greater than 1.25 D and less than 2.5 D.

Figure 14:
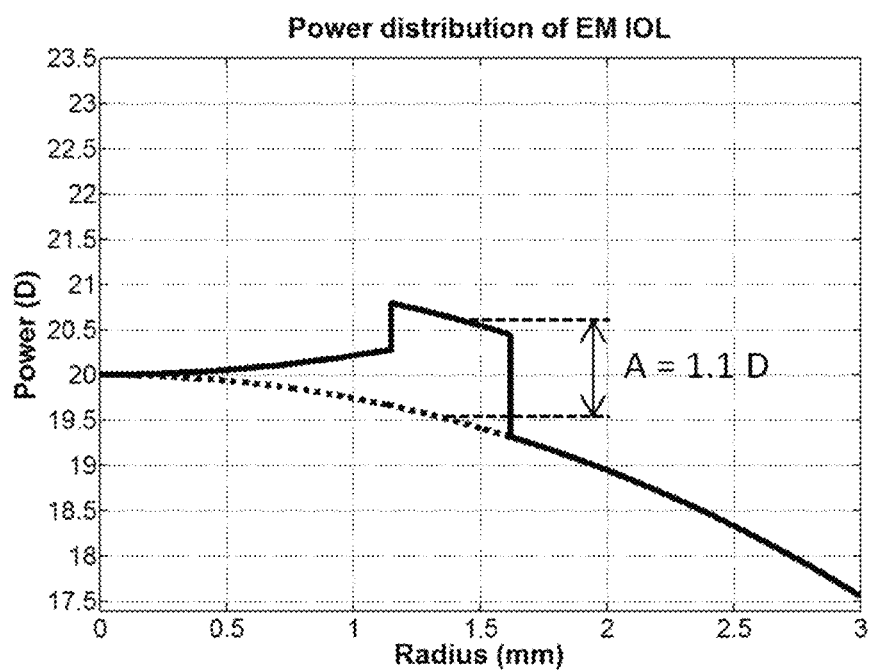
FIG. 14 is a plot showing a refractive power (vertical axis) provided by an optical part of an EM IOL in which a positive constant power of 1.1 D is added, versus a distance (horizontal axis) from the lens center O of the EM-IOL.

FIG. 14 is a plot showing a refractive power (vertical axis) provided by an optical part of an EM IOL in which a positive constant power of 1.1 D is added, versus a distance (horizontal axis) from the lens center O of the EM-IOL.

A power of 1.1 D in the present example is intended to correct the visual acuity of an aphakic patient for viewing an object located at an intermediate distance of approximately 1.2 m in front of the cornea.

Figure 15:
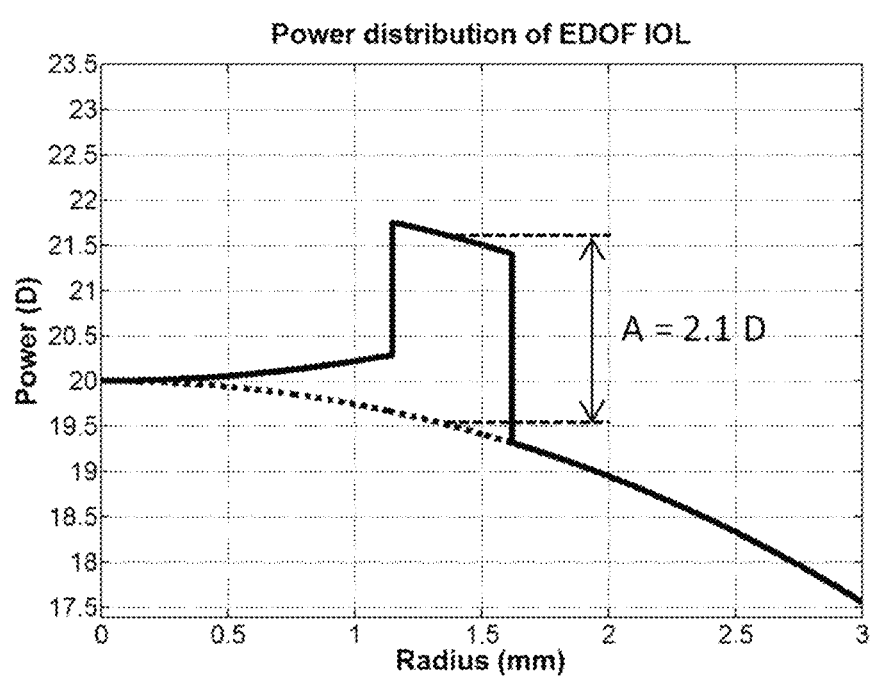
FIG. 15 is a plot showing a refractive power (vertical axis) provided by an optical part of an EDOF in which a positive constant power of 2.1 D is added, versus a distance (horizontal axis) from the lens center O of the EDOF.

FIG. 15 is a plot showing a refractive power (vertical axis) provided by an optical part of an EDOF in which a positive constant power of 2.1 D is added, versus a distance (horizontal axis) from the lens center O of the EDOF.

A power of 2.1 D in the present example is intended to correct the visual acuity of an aphakic patient for viewing an object located at an intermediate distance of approximately 65 cm in front of the cornea.

Figure 16:
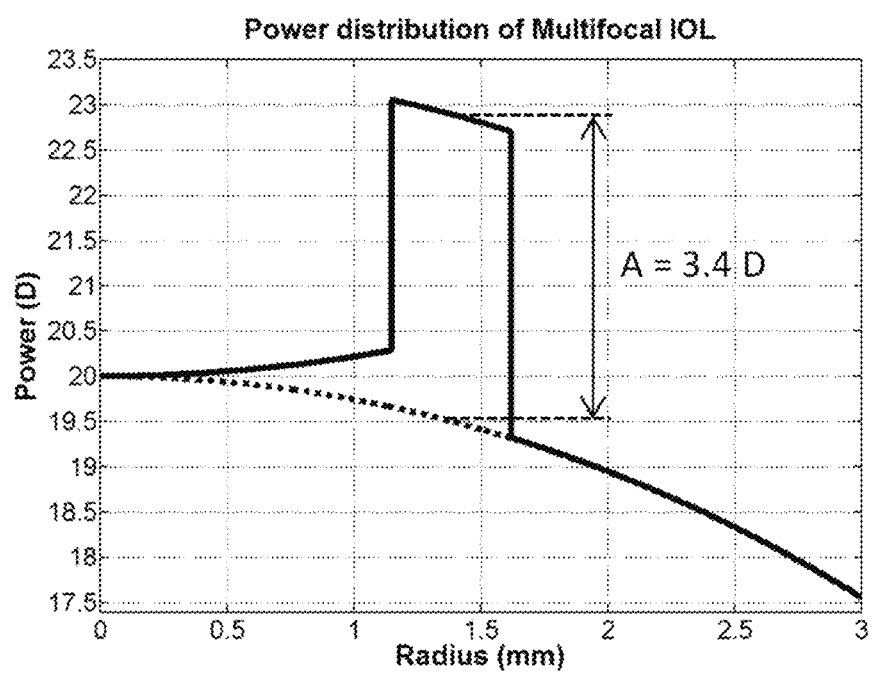
FIG. 16 is a plot showing a refractive power (vertical axis) provided by an optical part of a multifocal lens in which a positive constant power of 3.4 D is added, versus a distance (horizontal axis) from the lens center O of the multifocal lens.

FIG. 16 is a plot showing a refractive power (vertical axis) provided by an optical part of a multifocal lens in which a positive constant power of 3.4 D is added, versus a distance (horizontal axis) from the lens center O of the multifocal lens.

A power of 3.4 D in the present example is intended to correct the visual acuity of an aphakic patient for viewing an object located at a near distance of approximately 40 cm in front of the cornea.

Figure 17:
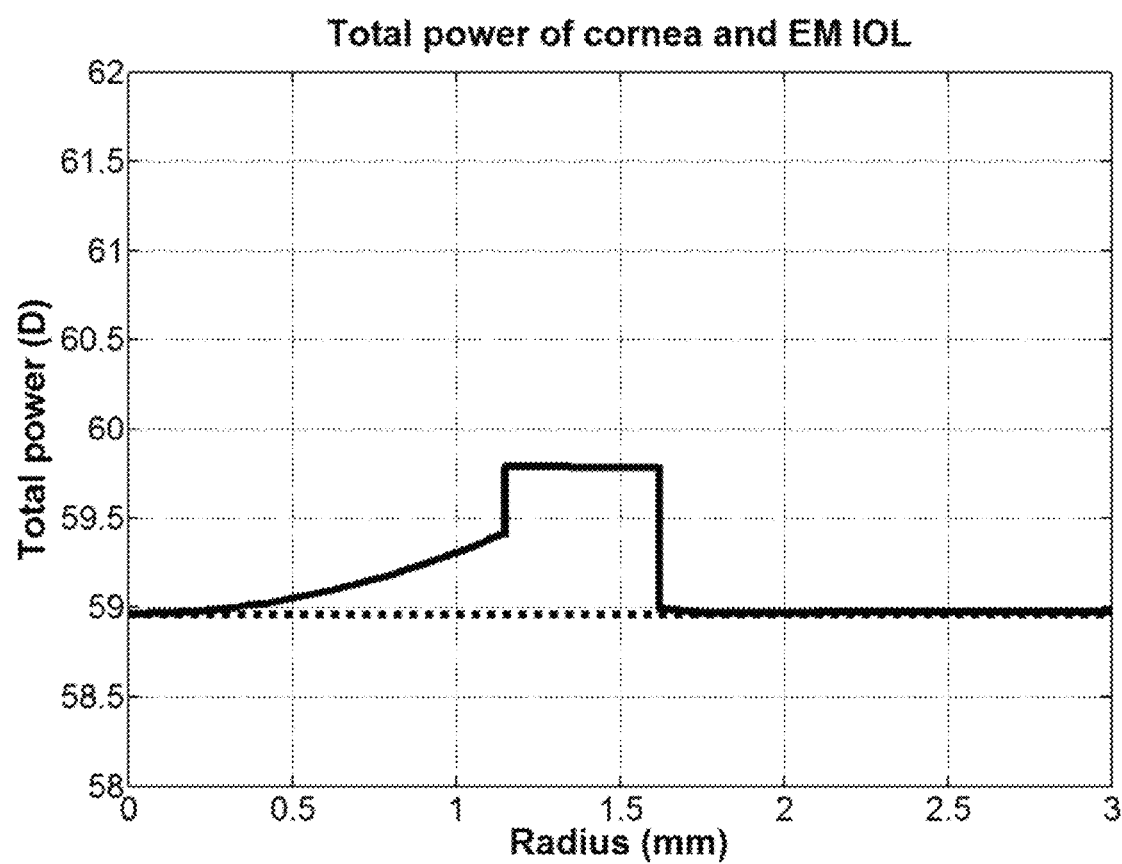
FIG. 17 is a plot showing a total power T (vertical axis) obtained by summing up the refractive power (vertical axis) of the cornea and the refractive power of the EM IOL in which a positive constant power of 1.1 D is added, versus a distance (horizontal axis) from the lens center O of the EM-IOL.

FIG. 17 is a plot showing a total power T (vertical axis) obtained by summing up the refractive power (vertical axis) of the cornea and the refractive power of the EM IOL in which a positive constant power of 1.1 D is added, versus a distance (horizontal axis) from the lens center O of the EM-IOL.

Figure 18:
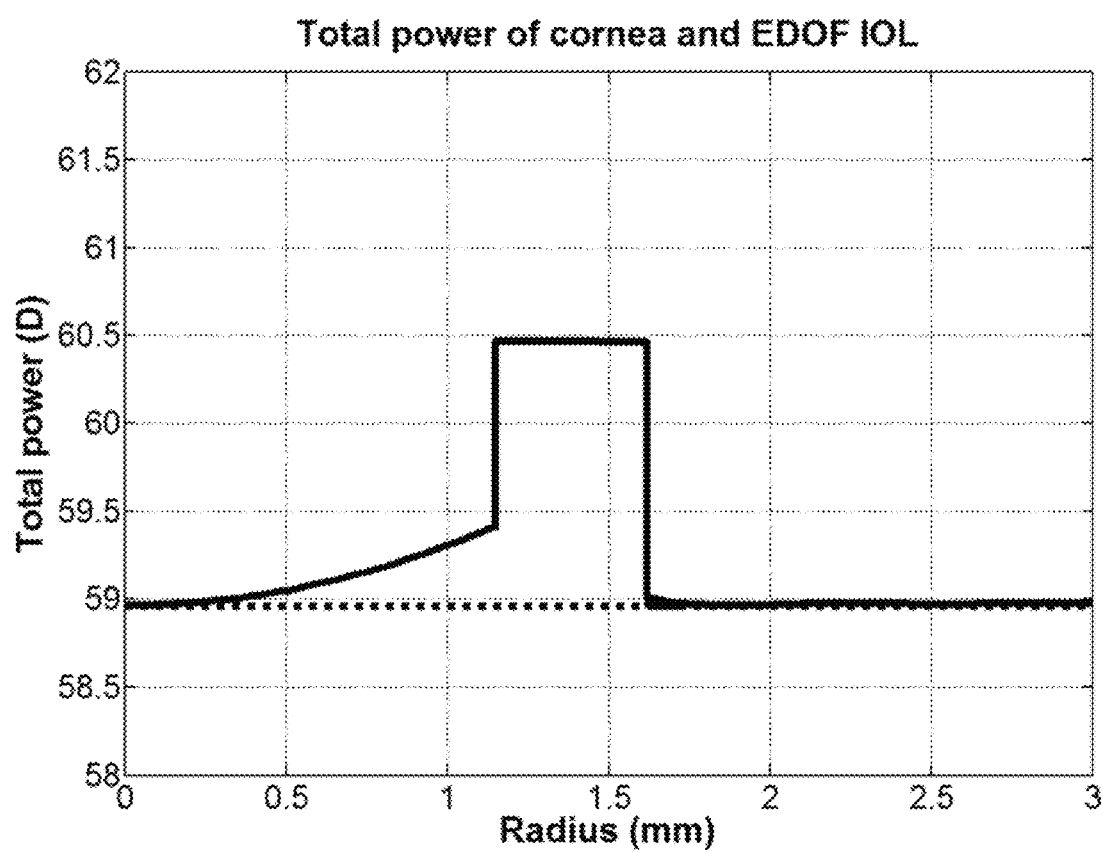
FIG. 18 is a plot showing a total power T (vertical axis) obtained by summing up the refractive power (vertical axis) of the cornea and the refractive power of the EDOF in which a positive constant power of 2.1 D is added, versus a distance (horizontal axis) from the lens center O of the EDOF.

FIG. 18 is a plot showing a total power T (vertical axis) obtained by summing up the refractive power (vertical axis) of the cornea and the refractive power of the EDOF in which a positive constant power of 2.1 D is added, versus a distance (horizontal axis) from the lens center O of the EDOF.

Figure 19:
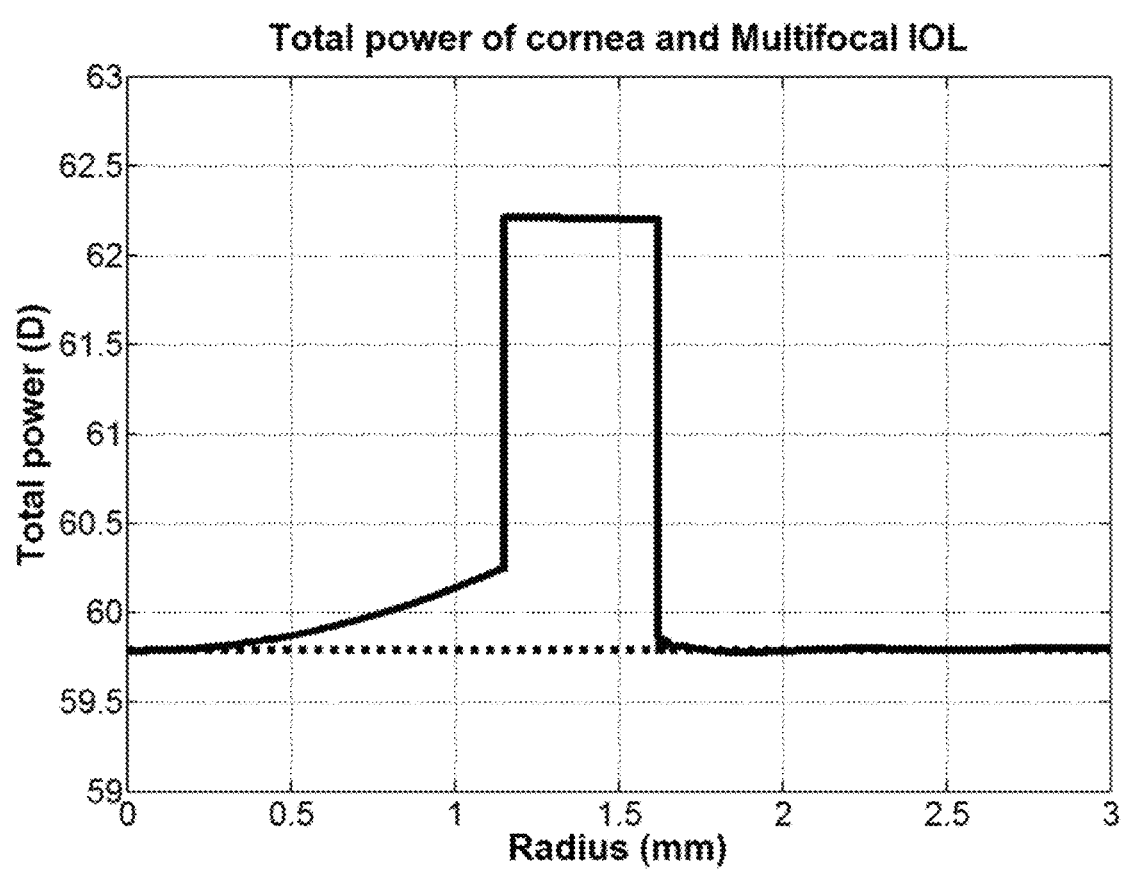
FIG. 19 is a plot showing a total power T (vertical axis) obtained by summing up the refractive power (vertical axis) of the cornea and the refractive power of the multifocal lens in which a positive constant power of 3.4 D is added, versus a distance (horizontal axis) from the lens center O of the multifocal lens.

FIG. 19 is a plot showing a total power T (vertical axis) obtained by summing up the refractive power (vertical axis) of the cornea and the refractive power of the multifocal lens in which a positive constant power of 3.4 D is added, versus a distance (horizontal axis) from the lens center O of the multifocal lens.

In FIGS. 17 to 19, the power is relatively constant at a radius in the range from approximately 1.15 mm to approximately 1.6 mm, and this region is an optical region of each of the intraocular lenses, and is a region in which a positive constant power is added.

Figure 20:
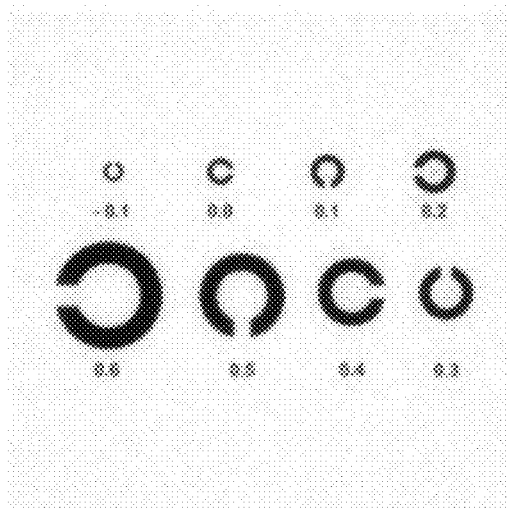
FIG. 20 shows simulated images reconstructed using an optical system constituted by the EM IOL according to FIGS. 14 and 17.
Figure 20:
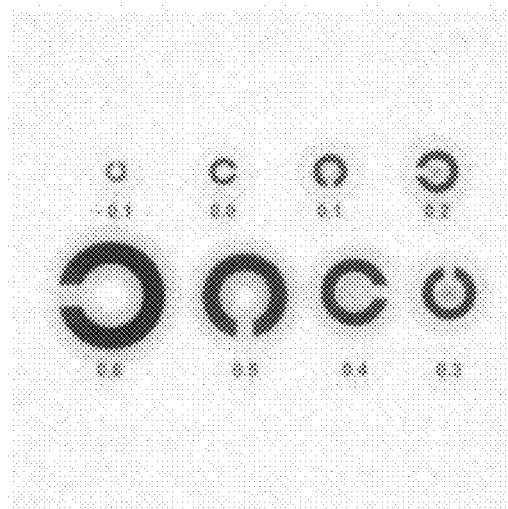
Figure 20:
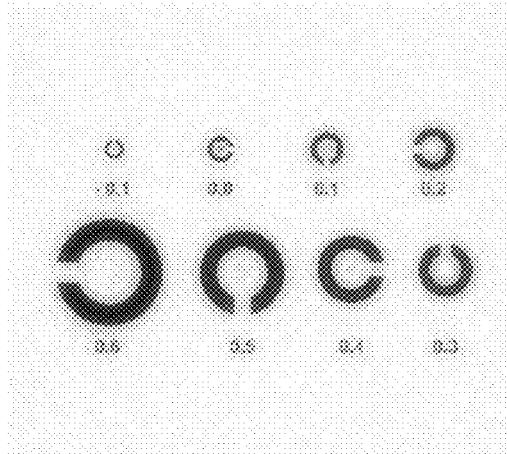
Figure 20:
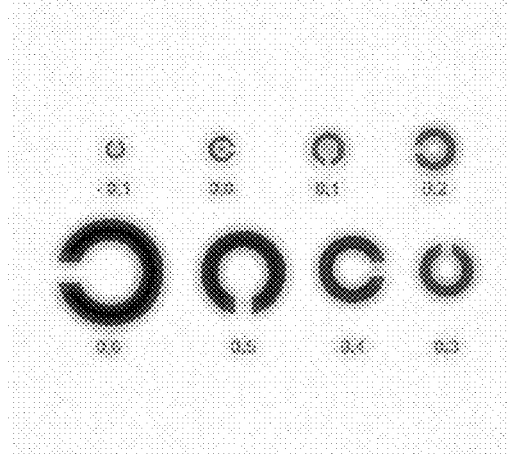

FIG. 20 shows simulated images reconstructed using an optical system constituted by the EM IOL according to FIGS. 14 and 17, wherein FIG. 20(a) is a diagram in which Landolt C chart are located at a distance of 6 m in front of the cornea, and the aperture diameter (pupil diameter) is set to 2.5 mm, FIG. 20(b) is a diagram in which Landolt C chart are located at a distance of 6 m in front of the cornea, and the aperture diameter (pupil diameter) is se to 3 mm, FIG. 20(c) is a diagram in which Landolt C chart are located at a distance of 1.2 m in front of the cornea, and the aperture diameter (pupil diameter) is set to 3 mm, and FIG. 20(d) is a diagram in which Landolt C chart are located at a distance of 1.2 m in front of the cornea, and the aperture diameter (pupil diameter) is set to 3.5 mm.

Referring to FIG. 20, it can be seen that, with the EM IOL having the power distribution shown in FIGS. 14 and 17, the visual acuity of the aphakic patient can be corrected at both a far distance (6 m in the present example) and an intermediate distance (1.2 m in the present example).

Figure 21:
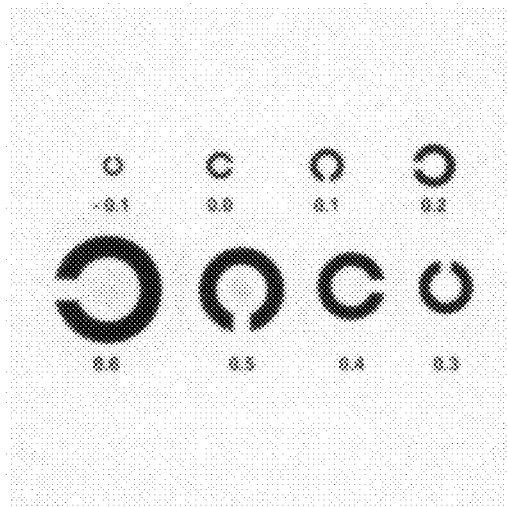
FIG. 21 shows simulated images reconstructed using an optical system constituted by the EDOF according to FIGS. 15 and 18.
Figure 21:
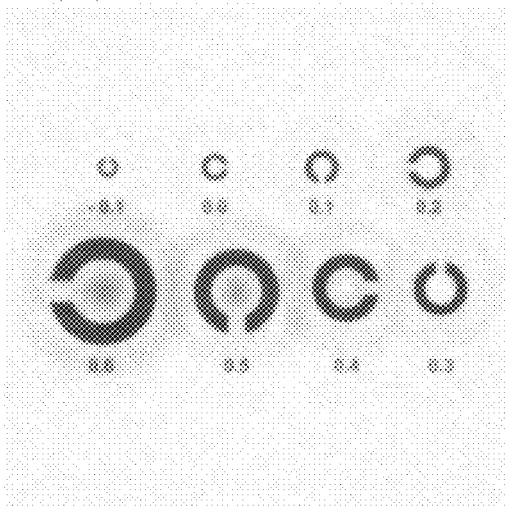
Figure 21:
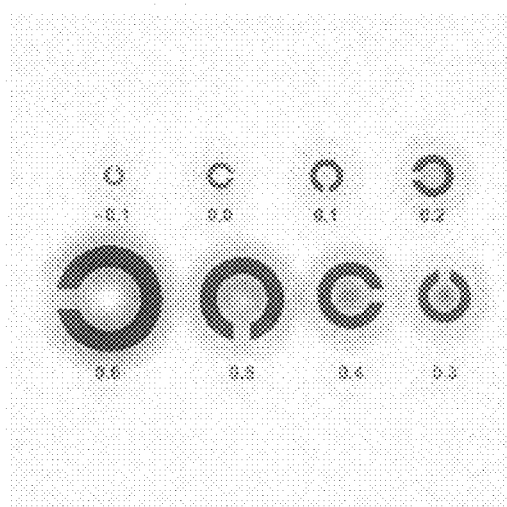
Figure 21:
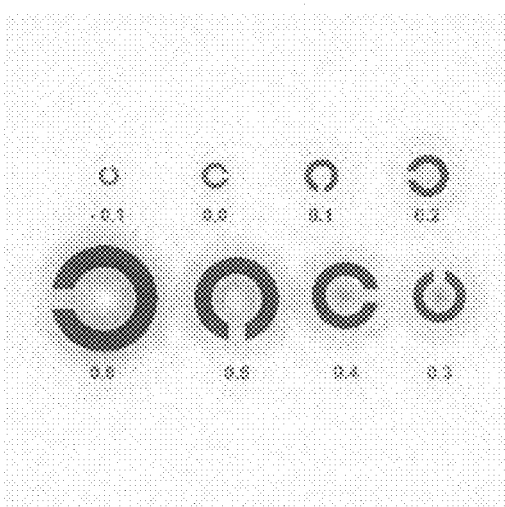

FIG. 21 shows simulated images reconstructed using an optical system constituted by the EDOF according to FIGS. 15 and 18, wherein FIG. 21(a) is a diagram in which Landolt C chart are located at a distance of 6 m in front of the cornea, and the aperture diameter (pupil diameter) is set to 2.5 mm, FIG. 21(b) is a diagram in which Landolt C chart are located at a distance of 6 m in front of the cornea, and the aperture diameter (pupil diameter) is se to 3 mm, FIG. 21(c) is a diagram in which Landolt C chart are located at a distance of 65 cm in front of the cornea, and the aperture diameter (pupil diameter) is set to 3 mm, and FIG. 21(d) is a diagram in which Landolt C chart are located at a distance of 65 cm in front of the cornea, and the aperture diameter (pupil diameter) is set to 3.5 mm.

Referring to FIG. 21, it can be seen that, with the EDOF having the power distribution shown in FIGS. 15 and 18, the visual acuity of the aphakic patient can be corrected at both a far distance (6 m in the present example) and an intermediate distance (65 cm in the present example).

Figure 22:
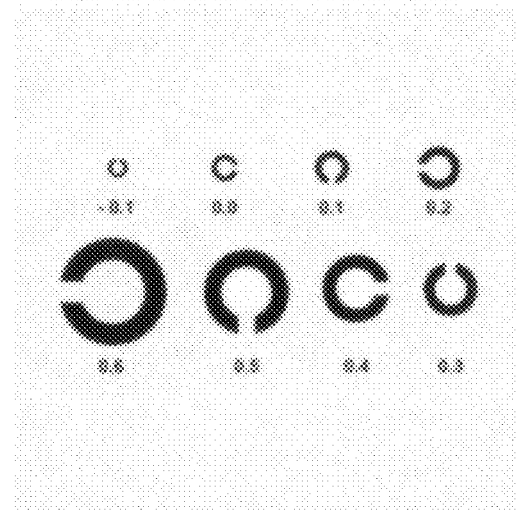
FIG. 22 shows simulated images reconstructed using an optical system constituted by the multifocal lens according to FIGS. 16 and 19.
Figure 22:
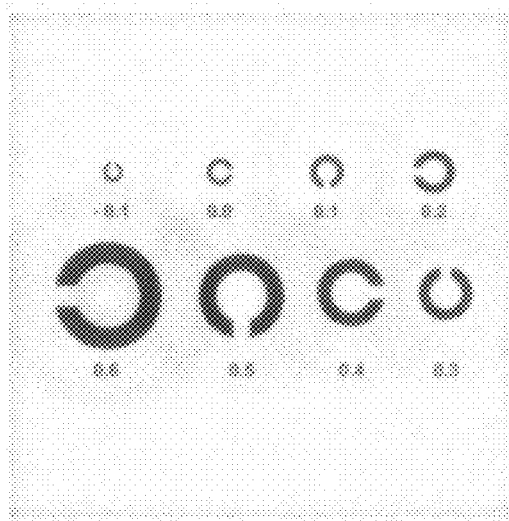
Figure 22:
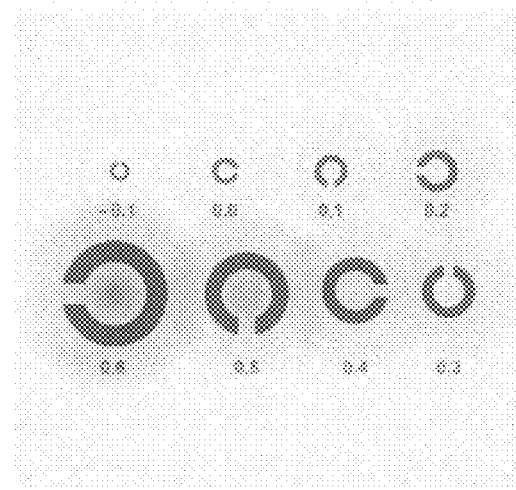
Figure 22:
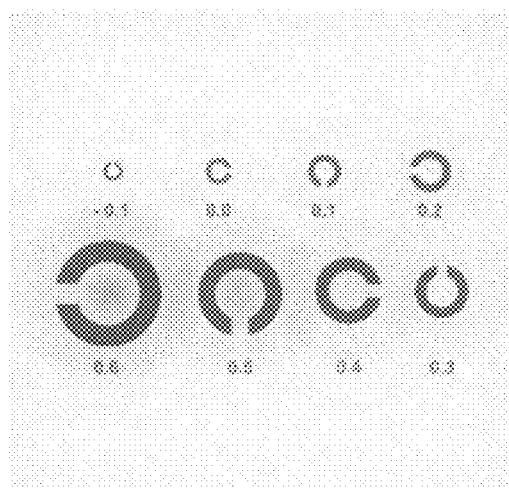

FIG. 22 shows simulated images reconstructed using an optical system constituted by the multifocal lens according to FIGS. 16 and 19, wherein FIG. 22(a) is a diagram in which Landolt C chart are located at a distance of 6 m in front of the cornea, and the aperture diameter (pupil diameter) is set to 2.5 mm, FIG. 22(b) is a diagram in which Landolt C chart are located at a distance of 6 m in front of the cornea, and the aperture diameter (pupil diameter) is se to 3 mm, FIG. 22(c) is a diagram in which Landolt C chart are located at a distance of 40 cm in front of the cornea, and the aperture diameter (pupil diameter) is set to 3 mm, and FIG. 22(d) is a diagram in which Landolt C chart are located at a distance of 40 cm in front of the cornea, and the aperture diameter (pupil diameter) is set to 3.5 mm.

Referring to FIG. 22, it can be seen that, with the multifocal lens having the power distribution shown in FIGS. 16 and 19, the visual acuity of the aphakic patient can be corrected at both a far distance (6 m in the present example) and a near distance (40 cm in the present example).

Each of the simulated images were obtained using an optical design software ZEMAX (registered trademark).

Referring to FIGS. 20, 21, and 22, a light shade surrounding each of the Landolt C chart is seen. This shade is generated by light rays that do not focus on the image plane (retina).

For example, the simulated image of FIG. 20(b), namely, the simulated image at an object distance of 6 m and a pupil diameter of 3 mm is obtained as a result of acute Landolt C chart (black or dark Landolt C chart) being reconstructed by light rays from Landolt C chart disposed at a far distance, and the light rays being focused on the retina by the first region (zone 1) for correcting the visual acuity for far vision in the EM-IOL. The light shade around each of the acute Landolt C chart is generated as a result of the light rays from the far distance not being focused by the second region (zone 2) for correcting the visual acuity for near vision.

On the other hand, the simulated image of FIG. 20(c), namely, the simulated image at an object distance 1.2 m and a pupil diameter 3 mm is obtained as a result of acute Landolt C chart (black or dark Landolt C chart) being reconstructed by light rays from Landolt C chart disposed at the intermediate distance, and the light rays being focused on the retina by the second region (zone 2) for correcting the visual acuity for intermediate vision in the EM-IOL. The light shade around each of the acute Landolt C chart is generated as a result of the light rays from the intermediate distance not being focused by the first region (zone 1) for correcting the visual acuity for far vision.

Referring to FIGS. 20, 21, and 22, a light shade surrounding each of the Landolt C chart is seen. However, the light shade is not generated on a retina image obtained from an aphakic patient being implanted with the EM-IOL, the EDOF, or the multifocal lens. This is due to a psychophysical mechanism by which the visual system of an aphakic patient adjusts and improves the appearance of an object that the patient wishes to see, but restricts or minimizes the appearance of light shade that the patient does not wish to see. This psychophysical mechanism enables an aphakic patient to adjust the focal point so as to ignore the appearance of the light shade (unwanted image), and to see only things that the patient wishes to see. As a result, an aphakic patient being implanted with the intraocular lens described in the present specification is able to see a target object clearly, sharply, and easily for far vision, intermediate vision, or near vision.

Approximately 1.2 m is set as an intermediate vision distance in the EM IOL according to FIG. 20, approximately 65 cm is set as an intermediate vision distance in the EDOF according to FIG. 21, and approximately 40 cm is set as the near vision distance in the multifocal lens according to FIG. 22.

A value other than the spherical aberration value (exemplary value in the present specification: 0.16 μm) of the cornea model described in Embodiment 1 may be used, and the value other than the spherical aberration value may be applied to the EM-IOL, the EDOF, and the multifocal lens described above.

A case where the technical idea of the present invention is applied to a monofocal lens is mainly illustrated in each of the embodiments. With the technical idea of the present invention, if a good result is obtained in a monofocal lens, based on which a multifocal lens is formed, the same technical idea can be easily applied to a multifocal lens. Consequently, the time required to develop a multifocal lens can be significantly reduced. In this respect as well, the technical idea of the present invention is very useful.

As shown in FIGS. 4A, 5A, 6A, 7A, 8A, and 9A and FIGS. 4B, 5B, 6B, 7B, 8B, and 9B, which represent the effects of Embodiment 1, the conditions are changed according to the aperture diameter (pupil diameter). Alternatively viewed, this can be considered that the lens function provided by the lens body is changed according to the aperture diameter.

For example, a lens function (e.g., an aperture diameter of 4.5 mm or more) taking a predetermined distance between near vision and intermediate vision into account is provided in a dark region in which the aperture diameter is large, and a lens function (e.g., an aperture diameter of 3 mm or less) taking a predetermined distance between far vision and intermediate vision into account is provided in a bright region in which the aperture diameter is small.

Furthermore, the bright region can be further divided into two bright regions. Specifically, a lens function specifically designed for viewing an object at a predetermined distance is provided in one of the bright regions that is relatively dark, and a function that is focused on far vision, while also taking viewing of an object at a predetermined distance into account, is provided in the other bright region that is relatively bright. At that time, the fact that a patient after a cataract surgery tends to be myopic is also taken into consideration.

The configuration created taking the above-described concept and modifications into account is as follows.

"An ophthalmic lens wherein a depth of focus in a small aperture diameter region that is a region in which the lens center O is disposed and that corresponds to an aperture diameter a1 is substantially the same as or deeper than a depth of focus of a small aperture diameter region of a virtual spherical lens having a curvature at a lens center, a medium aperture diameter region that is covered when the aperture diameter increases from the aperture diameter a1 to an aperture diameter a2 has a power corresponding to a predetermined finite distance (which can be set to a plurality of different distances) when the ophthalmic lens is being worn, and a large aperture diameter region that is covered when the aperture diameter increases from the aperture diameter a2 to an aperture diameter a3 has a power corresponding to far vision, and includes a negative longitudinal spherical aberration that cancels at least part of a positive longitudinal spherical aberration caused by the cornea when the ophthalmic lens is being worn."

The aperture diameters a1, a2, and a3 may be the aperture diameters described as the effects of Embodiment 1. That is, the aperture diameters a1, a2, and a3 may be set within a range that satisfies a1≤2.5 mm, 3 mm≤a2≤4 mm, and a3≥5 mm.

The small aperture diameter region corresponding to the aperture diameter a1 corresponds to the first region in the embodiments. The medium aperture diameter region that is covered when the aperture diameter increases from the aperture diameter a1 to the aperture diameter a2 corresponds to the second region in the embodiments. The large aperture diameter region that is covered when the aperture diameter increases from the aperture diameter a2 to the aperture diameter a3 corresponds to the third region in the embodiments.

The invention claimed is:

1. An intraocular lens comprising
at least three visual acuity correction regions that are concentric with a lens center O at which a predetermined base power is set, and that are adjacent to each other,
wherein the visual acuity correction regions are set as a first region including the lens center O, and a second region and a third region disposed in this order radially from the first region,
when r1 is a position of a first boundary between the first region and the second region, and r2 is a position of a second boundary between the second region and the third region, as viewed radially from the lens center O,
the first region is a region for correcting a visual acuity for far vision or a visual acuity for vision between far vision and intermediate vision,
the second region is a region for correcting a visual acuity for intermediate vision or a visual acuity for near vision,
the third region is a region for correcting the visual acuity for far vision,
a change in power is discontinuous on the first boundary and the second boundary,
a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary,
an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O to the position r1,
the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by a cornea,
the power is reduced in the third region so as to provide a negative longitudinal spherical aberration that cancels at least part of the positive longitudinal spherical aberration caused by the cornea,
a second step value constituted by a value obtained by subtracting a power $P_{B2Low}$ of the third region from a power $P_{B2High}$ of the second region on the second boundary is greater than a first step value constituted by a value obtained by subtracting the power $P_{B1Low}$ of the first region from the power $P_{B1High}$ of the second region on the first boundary, and
the power $P_{B2High}$ of the second region on the second boundary is greater than the base power, and the power $P_{B2Low}$ of the third region on the second boundary is less than the base power.

2. The intraocular lens according to claim 1,
wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

3. An intraocular lens comprising
at least three visual acuity correction regions that are concentric with a lens center O at which a predetermined base power is set, and that are adjacent to each other,
wherein the visual acuity correction regions are set as a first region including the lens center O, and a second region and a third region disposed in this order radially from the first region,
when r1 is a position of a first boundary between the first region and the second region, r2 is a position of a second boundary between the second region and the third region, and r3 is a position of an outermost edge of the third region, as viewed radially from the lens center O,
the first region is a region for correcting a visual acuity for far vision or a visual acuity for vision between far vision and intermediate vision,
the second region is a region for correcting a visual acuity for intermediate vision or a visual acuity for near vision,
the third region is a region for correcting the visual acuity for far vision,
a change in power is discontinuous on the first boundary and the second boundary,
a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary,
an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O from to the position r1,
a power $P_{B2High}$ of the second region on the second boundary is greater than the base power, and a power $P_{B2Low}$ of the third region on the second boundary is less than the base power, and the first region, the second region, and the third region are shaped such that a total power T obtained by summing up a refractive power of the cornea and a power of the intraocular lens increases in an area from the lens center O to the position r1 of the first boundary, the total power T is equal to a total power $T_o$ at the lens center O in an area from the position r2 of the second boundary to the position r3 of the outermost edge of the third region, and the total power T is equal to a value resulting from adding one or more positive constant powers to the total power $T_o$ in an area from the position r1 of the first boundary to the position r2 of the second boundary.

4. The intraocular lens according to claim 3, wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

5. An intraocular lens comprising
at least three visual acuity correction regions that are concentric with a lens center O at which a predetermined base power is set, and that are adjacent to each other,
wherein the visual acuity correction regions are set as a first region including the lens center O, and a second region and a third region disposed in this order radially from the first region,
when r1 is a position of a first boundary between the first region and the second region, and r2 is a position of a second boundary between the second region and the third region, as viewed radially from the lens center O,
the first region is a region for correcting a visual acuity for far vision or a visual acuity for vision between far vision and intermediate vision,
the second region is a region for correcting a visual acuity for intermediate vision or a visual acuity for near vision,
the third region is a region for correcting the visual acuity for far vision,
a change in power is discontinuous on the first boundary and the second boundary,
a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary,
an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O to the position r1,
a power $P_{B2High}$ of the second region on the second boundary is greater than the base power, and a power $P_{B2Low}$ of the third region on the second boundary is less than the base power, and
the first region and the second region are sized such that, assuming that all light rays for a spatial frequency of 50 line pairs/mm pass through a virtual cornea and the intraocular lens, a depth of focus is substantially the same as or deeper than a depth of focus of the virtual spherical lens for an aperture diameter of 2.5 mm or less,
a depth of focus is at least 10% deeper than the depth of focus of the virtual spherical lens for an aperture diameter of 3 to 4 mm, and
a contrast peak is present at a defocus value in a range from −0.25 D to 0.25 D for an aperture diameter of 5 mm or more.

6. The intraocular lens according to claim 5, wherein the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by a cornea.

7. The intraocular lens according to claim 6, wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

8. The intraocular lens according to claim 5, wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

9. An intraocular lens comprising
at least three visual acuity correction regions that are concentric with a lens center O at which a predetermined base power is set, and that are adjacent to each other,
wherein the visual acuity correction regions are set as a first region including the lens center O, and a second region and a third region disposed in this order radially from the first region,
when r1 is a position of a first boundary between the first region and the second region, and r2 is a position of a second boundary between the second region and the third region, as viewed radially from the lens center O,
the first region is a region for correcting a visual acuity for far vision or a visual acuity for vision between far vision and intermediate vision,
the second region is a region for correcting a visual acuity for intermediate vision or a visual acuity for near vision,
the third region is a region for correcting the visual acuity for far vision,
a change in power is discontinuous on the first boundary and the second boundary,
a base difference value (exceeding 0 D) obtained by subtracting the base power from a power $P_{B1Low}$ of the first region on the first boundary is less than 50% of a base difference value (exceeding 0 D) obtained by subtracting the base power from a power $P_{B1High}$ of the second region on the first boundary,
an average value (exceeding 0 D) of the base difference values within the first region from the lens center O to the position r1 of the first boundary is greater than 5 times an average value (exceeding 0 D) of the base difference values within the first region from a lens center O of a virtual spherical lens having a base power at the lens center O to the position r1, a power $P_{B2High}$ of the second region on the second boundary is greater than the base power, and a power $P_{B2Low}$ of the third region on the second boundary is less than the base power, and the power is reduced in the third region so as to provide a negative longitudinal spherical aberration that cancels at least part of a positive longitudinal spherical aberration caused by a cornea, a sag value of an anterior surface, a sag value of a posterior surface, or sag values of both the anterior surface and the posterior surface of the intraocular lens are represented by the following polynomial equation:

$$z = \frac{cr^2}{1+\sqrt{1-(1+k)c^2r^2}} + a_1r^2 + a_2r^4 + a_3r^6 + a_4r^8 + \ldots + a_n r^{2n} \quad \text{[Math. 1]}$$

Z: sag value
c: curvature of lens center (=1/R[m])
k: conic constant
r: distance from lens center, i.e., radius
$a_1, a_2, \ldots, a_{n-1}, a_n$: coefficient
the power of each of the regions is represented by the following polynomial equation:

$$P_i = c_{0,i} + c_{1,i}r^1 + c_{2,i}r^2 + c_{3,i}r^3 + c_{4,i}r^4 + \ldots + c_{n,i}r^n \quad \text{[Math. 2]}$$

$P_i$: power of i-th region
r: distance from lens center, i.e., radius
$c_{0,i}, c_{1,i}, \ldots, c_{n-1,i}, c_{n,i}$: coefficient
the power of the second region is represented by the following equation:

$$P_2 = A + P_3 \quad \text{[Math. 3]}$$

$P_2$: power of second region
$P_3$: power of third region
A: addition power relative to reference aspheric power
A is a value obtained by subtracting, from the power of the second region at a predetermined position r within the second region, a reference aspheric power, at the position r, of a virtual aspheric lens that has a base power at the lens center O, and that cancels the whole of the positive longitudinal spherical aberration caused by the cornea, and
the power of the third region is represented by the following polynomial equation:

$$P_3 = c_{0,3} + c_{1,3}r^1 + c_{2,3}r^2 + c_{3,3}r^3 + c_{4,3}r^4 + \ldots + c_{n,3}r^n \quad \text{[Math. 4]}$$

$P_3$: power of third region
r: distance from lens center, i.e., radius
$c_{0,3}, c_{1,3}, \ldots, c_{n-1,3}, c_{n,3}$: coefficient.

10. The intraocular lens according to claim 9,
wherein, in an area from the position r1 of the first boundary to the position r2 of the second boundary, a total power T obtained by summing up the refractive power of the cornea and the power of the intraocular lens is constituted by one or more constant values, and a visual acuity when viewing an object at one or more distances from an intermediate vision distance to a near vision distance is corrected using the total power T.

11. The intraocular lens according to claim 10,
wherein the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by a cornea.

12. The intraocular lens according to claim 11,
wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

13. The intraocular lens according to claim 10,
wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

14. The intraocular lens according to claim 9,
wherein the second region has a power resulting from adding one or more positive constant powers to a reference aspheric power, in an area from the position r1 to the position r2, of a virtual aspheric lens that has a base power at the lens center O, and that cancels the whole of a positive longitudinal spherical aberration caused by a cornea.

15. The intraocular lens according to claim 14,
wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

16. The intraocular lens according to claim 9,
wherein an area from the position r2 of the second boundary to a position r3 of an outermost edge of the third region as viewed radially from the lens center O has a power equal to a reference aspheric power, from the position r2 to the position r3, of a virtual aspheric lens that has a base power at the lens center O, and that cancels the whole of a positive longitudinal spherical aberration caused by a cornea.

\* \* \* \* \*

UNITED STATES PATENT AND TRADEMARK OFFICE
CERTIFICATE OF CORRECTION

PATENT NO. : 12,257,143 B2
APPLICATION NO. : 17/779311
DATED : March 25, 2025
INVENTOR(S) : Demas Sanger Page 1 of 1

It is certified that error appears in the above-identified patent and that said Letters Patent is hereby corrected as shown below:

On the Title Page

In Item (71), "Sinapore" should read --Singapore--.

Signed and Sealed this
Twenty-second Day of April, 2025

Coke Morgan Stewart
*Acting Director of the United States Patent and Trademark Office*